United States Patent
Deleon et al.

(10) Patent No.: US 12,371,706 B2
(45) Date of Patent: Jul. 29, 2025

(54) METHODS OF IDENTIFYING, SELECTING, AND PRODUCING ANTHRACNOSE STALK ROT RESISTANT CROPS

(71) Applicant: PIONEER HI-BRED INTERNATIONAL, INC., Johnston, IA (US)

(72) Inventors: Alyssa Marie Deleon, Des Moines, IA (US); Kevin A Fengler, Clive, IA (US); Shawn Thatcher, Urbandale, IA (US); Petra J Wolters, Kennett Square, PA (US); Mark Timothy Jung, Urbandale, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 352 days.

(21) Appl. No.: 17/636,060

(22) PCT Filed: Aug. 17, 2020

(86) PCT No.: PCT/US2020/046665
§ 371 (c)(1),
(2) Date: Feb. 17, 2022

(87) PCT Pub. No.: WO2021/041077
PCT Pub. Date: Mar. 4, 2021

(65) Prior Publication Data
US 2022/0282338 A1 Sep. 8, 2022

Related U.S. Application Data

(60) Provisional application No. 62/890,729, filed on Aug. 23, 2019.

(51) Int. Cl.
*C12N 15/82* (2006.01)
*C12Q 1/6895* (2018.01)

(52) U.S. Cl.
CPC ....... *C12N 15/8282* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,082,991 A | 1/1992 | Cavanah | |
| 7,317,154 B2 | 1/2008 | Colbert et al. | |
| 10,202,655 B2 * | 2/2019 | Broglie | C07K 14/415 |
| 2016/0355840 A1 | 12/2016 | Davis et al. | |
| 2017/0114356 A1 * | 4/2017 | Li | C07K 14/415 |
| 2022/0142075 A1 | 5/2022 | Davis et al. | |

FOREIGN PATENT DOCUMENTS

| | | | |
|---|---|---|---|
| WO | WO/2015/088970 | 6/2014 | |
| WO | WO-2015088970 A1 * | 6/2015 | C12Q 1/68 |
| WO | WO/2016/196269 | 12/2016 | |

OTHER PUBLICATIONS

International Application Search Report and Written Opinion, European Patent Office, 2020-13-20.
Toman, et al., Inheritance of Resistance to Anthracnose Stalk Rot of Corn, The American Phytopathological Society, US (1993) vol. 83(9) pp. 981-986.
International Preliminary Report on Patentability for International Application No. PCT/US2020/046665, mailed Mar. 3, 2022, 8 Pages.

* cited by examiner

*Primary Examiner* — Cynthia E Collins

(57) ABSTRACT

The field is related to plant breeding and methods of identifying and selecting plants with resistance to anthracnose stalk rot. Provided are methods to identify novel genes that encode proteins providing plant resistance to anthracnose stalk rot and uses thereof. These disease resistant genes are useful in the production of resistant plants through breeding, transgenic modification, or genome editing.

4 Claims, 1 Drawing Sheet
Specification includes a Sequence Listing.

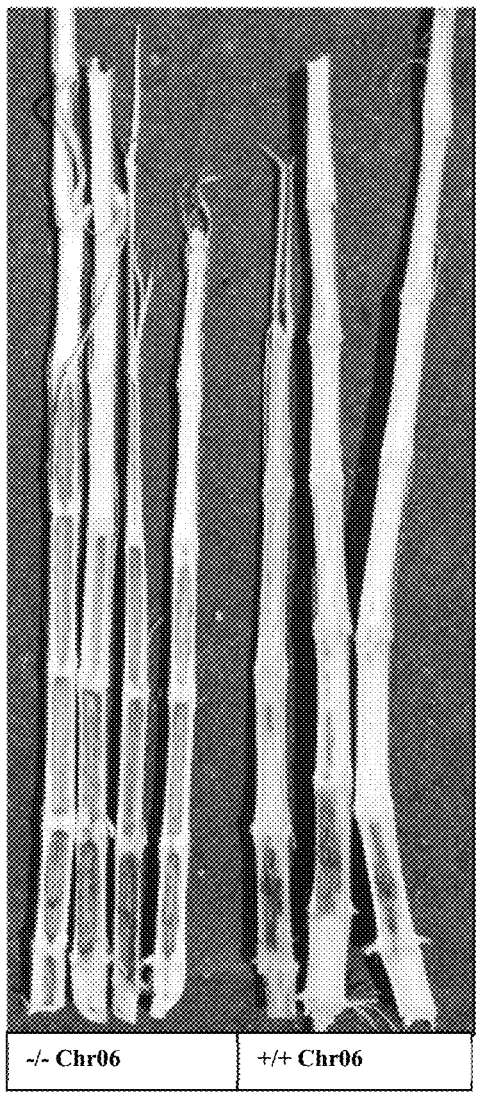

SEQUENCE LISTING

```
<160> NUMBER OF SEQ ID NOS: 9

<210> SEQ ID NO 1
<211> LENGTH: 6102
<212> TYPE: DNA
<213> ORGANISM: Zea mays

<400> SEQUENCE: 1
atggagttcg caactggagc gctaggcacc cttcttctca agctctccat gctgcttcat      60
ggtgagtaca acctggagaa gggcgtcagg ggggacatcc agcgcgtcat gaacaagctc     120
gagcgggttc attctgtcct cggccatgtt gtcgaagtgc ctgtgccact gaagccacgt     180
cctgatctgg tcagaatgtt ggcacgcagc gtcagggagc tatcctacga catggaggac     240
ttcgtcgaca ccttcctggt gcgtgtccaa ggccctgaac gcaccagcaa aagaagcgcc     300
aaaatattca tgaataagac atatatggtc gtgaatcgcc atgagatcgc ccagaccatc     360
aaggacttcg aagagcgcgt ccagcagata gatgagcgtc gtcaaaggta cgatgttgat     420
gctatggttc cccgtgtcaa aaccttggtt gatcctcgca tatttgctct gaagtacacc     480
aaggccacgg accttgtcgg catggatgag gcaagggagg aactaatcac aaggttgacc     540
aaggaagatg acacctccac tgaacaaagg cgagtctcta tcgttggttt tggaggactt     600
ggcaagacag cgcttgcaaa agcagtttat gacaaactta agctaaagg ggaattccat     660 tgcgcggcct ttgtgtcggt gtctcggttt cctcagctcg aaaaattctt caaggaattg     720
ctttatgagc ttgacgagac tgagtacaag gaacttattg acatcagcac cccattggaa     780
cttatgaatc tagtgcatga attccttcat aataagaggt accttattgc tgtcgatgac     840
atatgggata ctgacgcatg ggcaatgata caatgggctt ttcctgagaa taagctagga     900
agcagaataa tcgcaactac tcgcagaatt gatgttgctg agtatgtagg tggttgctat     960
atgatgaaac ctcttactcg agagaaatca aatatattat tctatggacg aatatttggc    1020
tctgaaggta aatgtcctcc tgaactttct gatgcgtctg agaaaatatt gaataaatgc    1080
ggaggcgtgc cattggctat tattactaca tctagcttgc tggctagtaa gtcaagaaac    1140
ataaaagaat ggtacaatgt tgctgattct attggttcca gaatactaaa aaacagtact    1200
gaaatggaga atttgaggaa catactgctg cttagctatt atgatctacc agcacgatta    1260
aagacatgtt tgttatatct gagtattttc cctgaagatt gtgagattgg gatgcatcgg    1320
ttaatatgga ggtggatagc tgaaggtttt ttcaatggag aactagcaca tgatgggctc    1380
tttaaccttg gcgaatcttg tttccacgag ctcataagaa gaagcatggt gcagccagta    1440
acacttgaag gcacgggtct tgtatatgct tgtcgtgttc ataatatgtt tcatgatttg    1500
atcctctaca tgtcacacga agaagaattt gtttctgcag tcaatgaaaa gtttggtctt    1560
ctagatgttc gttctcggcg gttagcattc cagaacataa caaaagagca gtacagactt    1620
```

```
gtggaacatc cacggctggc acaattgagg tcacttaatg ccattggatg tcctatatac    1680
gcgatacctc caattgaaag ctataaatta ttgcgtgtac tggatttcga aaattgtgca    1740
ggtattgaag gccatgatct tgttcatctt gggaaattgc atcacctcaa gttccttggg    1800
ctaagaaaca cgtttatcgg taagctgccg gaaggaatag ggaaccctcaa gtttctgcaa   1860 acattggacc tcgatggaac tggtgtggaa gaattacctc aagccttgca taatcttaca    1920
gaattgatgt gcctaattgc tgactggaga acgagagtgc ccaattggat tggtaacctc    1980
acgtccctgc agcacttggt gatttatcct ggtgggcatg acgatgagga ttctgcgagc    2040
aggtttgtta atgagctggg aaagctgaga caactaaggg tgctccgttt tttgataaaa    2100
gcacaagatg aagggcagct gagagatttg ctagagtccc tatcgaatct gccagagatc    2160
gaggctatac atttttgatta ctatggagta cagttaaaata gaggtgttca gttggaacct    2220
gaaggctatg ccctctctag acatattcgt tccatggaat tgcgctggtt ggagttctca    2280
aggctgcctc tttggattaa tcctggacaa cttcctaacc tctaccactt atggctgatg    2340
gtatctgatg cggaagagcg ggatctggaa atccttgggg ggtttccagt gcttcactcc    2400
ctccacttgt tgattgtgaa tactgaacgt gaagatgtca tgacttgtgg ctgtggtgga    2460
ttcaagaatt tgaaatgctg cagtataact aaaccgctga aatttgtaca tggagctatg    2520
cccaggcttg aagtcctcga ttttccatttc agtgtgcaac tcctaacgga ttcaaaccaa    2580
gaatttgatt ttgactttgg cttgggaaac ctacattggc ttcagcaagc catcgttcaa    2640
atcacagccc ttggtgagga ggtggagtct gtggggagag cacaggtggc tctgcgggat    2700
gcaatacgta cccatcccaa ccgtcctacc cttgaaataa acttatttgg gcaaacaata    2760
cctccagagt taccaaagca agacgacgat ggagcgaaaa ttgtggagat atcaccggcc    2820
gagagtagtc gtcaagctca agagcgggag aaaagaagca tcgatgtggc gacgaagaaa    2880
gcaacacggg tgccgtcttt ttacacaaag tcatcaattg atgagccaat ggatcagctc    2940
ataaacatgc tatctgtggt tgatgacgaa gcctacacta gaacataaa gatactatct    3000 attgtaaggt ctgagggact ggggaagact actctggccc aaaaagcatt cgaagagctc    3060
cattcgcaat ttgaccgtgg ggcgttcgtt ctactaggcc agaatcctga cttgaggaga    3120
gtctttgctg acattctccg tggtcttgac aagcaaaggt acatagattt cccagtggca    3180
atattggatc tagtggaccct gatctggcta gtccgtaaat cgctcataaa caaaaggttc    3240
tttattgtat ttgatgatat atgtgatgta aaagcatggg aaattataaa gtgcgctttg    3300
attgaaaata caaccacag tgtagttctt acgacaagtc gcaacactgg tattactgaa    3360
attattggtg gcagcaagca attacaacct ctatcagcaa ctatctctaa aaatctactc    3420
tgcaaaaggt tatttggatc ggcaggcaag tgtccttctg aactagtaaa tatatgtgac    3480
aatcttgtag aagaatgtgg tggaatacta tctgtgatcg acgaaactgt gacattgctt    3540
gcaagtatac caccaacagt ggagaactgg gaggcagtgt acgccagaag aatgttggat    3600
cggtcttatc ctggtttaac tgacagtcta aagaattgct tactctatttt tactatgttt    3660 cgaagaggac atgagattag tggagaacac ttaatatgtg catggatagc tgaaggtttt    3720
gtacatgggc aagaggtagc agagacctac cttagtgatc tagtaaaaaa gaaattaatc    3780
gatgcagtgg aggttgatgc tggaggaaag gtcctcacgt gccgcatgta tgacttggtg    3840
catgacttta tcgtctcaaa atcaattgaa gaacgatttg tttatatttt aaatgactcg    3900
gaaggcagag atttgtcaga agcagttcac gttcaccagc gactatacat ccaggggacat    3960
```

| | | | | | |
|---|---|---|---|---|---|
| aataacaaag | aactagacct | gcaaattcct | tggctgcccc | aagtgaagtc | acttgtctcc | 4020 |
| tgtggtactg | cgccatccat | cttaaagttt | aagggtctac | atgttatgga | tttaggggcc | 4080 |
| tgtgaatctt | tgcaggctag | tcatctcaag | ggtataaata | atgtaagttc | tttgagatat | 4140 |
| ctggtcatag | gaggtaagtg | tatctctggc | atccctaagg | aaattgcgaa | gctggaacat | 4200 |
| ttgcggacac | tagatttaag | tgcaagtggt | ctaaatgaat | tgccagaata | tgttttcatg | 4260 |
| ataagaaaat | tggaacgcct | aattgttaat | agtcagatga | agatatcata | tggtattgca | 4320 |
| aagatgtctg | ctttacagga | gctaggcgat | atcaatgtca | ccgacccaga | gttgctgaaa | 4380 |
| agtctctgta | agctaaccaa | attgagggtt | cttagaattt | ccatatggtc | atgggatgat | 4440 |
| agtttgaaga | actattttaa | caactgtgt | gacaacttgc | gttcactggt | tcagtgcacg | 4500 |
| gagaacatcc | agagtctctc | cataatgaca | tgctgctccc | tggttttcat | ggatgatttg | 4560 |
| ggtgagaatt | ggaccctca | atgtctccag | aagctcgagg | tcggttgcag | cgcatttgac | 4620 |
| atattgccaa | gttggtttgg | ctcactttct | agtatctcca | cgttaacaat | cgaggtctac | 4680 |
| aagctgtcac | aggacataat | tgatacgctc | ggaaggctgg | ctggtcttgg | ttctctatcc | 4740 |
| ctgacatcga | aacaagtacc | aaaaggatac | tttgtgatcg | gctctgacag | gttcaataag | 4800 |
| ctacagagct | taaagtttgt | gagcaatgca | atggtagaga | tgtttccacg | tcaacaatca | 4860 |
| aatggcacgg | aacagctcaa | aaggcttatg | attgtgttcc | atgcttcacg | tacacaagat | 4920 |
| gtgaacaaag | atttctgctt | tggtttggag | aacctgtctt | ccctagagca | tgttcgtgtt | 4980 |
| gaaataattt | gtttcgatgc | cagccataac | atggtgaaaa | acgcagaagc | tgcagttcag | 5040 |
| aaagctatat | ctggcacaag | tatcgcaaat | ctggaaatac | gaagacttca | ggaaaatagt | 5100 |
| atgacacagg | acgaagcgga | cctctgtgat | gcagtacaag | agcagaataa | tcagaagcac | 5160 |
| cagaaaatga | agagaattta | tgcaacgggg | gactggcaac | tggaaatagc | acatagttct | 5220 |
| atggagtccc | aggatgggta | cctcacttct | ttaccgaacc | aggaaagtgc | agatgttgtt | 5280 |
| ggctccgata | gtattgtgga | accactagtg | aatgaaatga | actcgcagac | aattaagagg | 5340 |
| gatcaatcca | cgaatttcag | tgaagatgag | gacttaatgt | tggtttctag | ctaccttaat | 5400 |
| gtaagcaaag | attctattac | tggaagggat | aaaaaagaag | gcacattttg | ggaaagagta | 5460 |
| tgggaatact | ataacaagaa | taggacattc | gagtccgatc | atagttggtc | gtcattgaaa | 5520 |
| catcgctggc | ttgcaattca | gaaggaagtg | aatatctttc | aaggttacta | tgatgccata | 5580 |
| gaaaggaaaa | atcaaagtgg | ccagacaagt | gatgacaagc | atgctgaagc | agaagtagaa | 5640 |
| ttccgagaaa | aacaagggaa | ggcttttttct | gtattccatg | tgtggatgat | tctaaggcat | 5700 |
| gagccaaagt | gggcatttag | agaatcaaag | atcaaagacc | agcatgaagc | aaacaatgct | 5760 |
| aatactgatg | ctcctgccaa | catttataga | ccacagggga | ggaaagctga | gaaggaaaag | 5820 |
| gctcgtgcga | gaaagcatgg | tggatctgat | gttgatggtg | atccgttcat | cgaagaagta | 5880 |
| aaaaatatga | gggaagcacg | ggaagaaaca | gaacgagacc | gaaagaccca | tgatgacaag | 5940 |
| ttctatgagt | tggaaaagag | taagcttgaa | ttggagcgag | atcgacatga | caagagata | 6000 |
| atgcaaacag | acacaagcac | aatggatgaa | gaatcgaaac | aatacttcaa | gttgatgaaa | 6060 |
| caagagattt | tggctcgccg | tttcgggagt | agtcagccat | ag | | 6102 |

<210> SEQ ID NO 2
<211> LENGTH: 2033
<212> TYPE: PRT
<213> ORGANISM: Zea mays

<400> SEQUENCE: 2

```
Met Glu Phe Ala Thr Gly Ala Leu Gly Thr Leu Leu Lys Leu Ser
1               5                   10                  15

Met Leu Leu His Gly Glu Tyr Asn Leu Glu Lys Gly Val Arg Gly Asp
            20                  25                  30

Ile Gln Arg Val Met Asn Lys Leu Glu Arg Val His Ser Val Leu Gly
        35                  40                  45

His Val Val Glu Val Pro Val Pro Leu Lys Pro Arg Pro Asp Leu Val
    50                  55                  60

Arg Met Leu Ala Arg Ser Val Arg Glu Leu Ser Tyr Asp Met Glu Asp
65                  70                  75                  80

Phe Val Asp Thr Phe Leu Val Arg Val Gln Gly Pro Glu Arg Thr Ser
                85                  90                  95

Lys Arg Ser Ala Lys Ile Phe Met Asn Lys Thr Tyr Met Val Val Asn
                100                 105                 110

Arg His Glu Ile Ala Gln Thr Ile Lys Asp Phe Glu Glu Arg Val Gln
    115                 120                 125

Gln Ile Asp Glu Arg Arg Gln Arg Tyr Asp Val Asp Ala Met Val Pro
    130                 135                 140

Arg Val Lys Thr Leu Val Asp Pro Arg Ile Phe Ala Leu Lys Tyr Thr
145                 150                 155                 160

Lys Ala Thr Asp Leu Val Gly Met Asp Glu Ala Arg Glu Glu Leu Ile
                165                 170                 175

Thr Arg Leu Thr Lys Glu Asp Asp Thr Ser Thr Glu Gln Arg Arg Val
                180                 185                 190

Ser Ile Val Gly Phe Gly Gly Leu Gly Lys Thr Ala Leu Ala Lys Ala
        195                 200                 205

Val Tyr Asp Lys Leu Lys Ala Lys Gly Glu Phe His Cys Ala Ala Phe
210                 215                 220

Val Ser Val Ser Arg Phe Pro Gln Leu Glu Lys Phe Phe Lys Glu Leu
225                 230                 235                 240

Leu Tyr Glu Leu Asp Glu Thr Glu Tyr Lys Glu Leu Ile Asp Ile Ser
                245                 250                 255

Thr Pro Leu Glu Leu Met Asn Leu Val His Glu Phe Leu His Asn Lys
            260                 265                 270

Arg Tyr Leu Ile Ala Val Asp Asp Ile Trp Asp Thr Asp Ala Trp Ala
    275                 280                 285

Met Ile Gln Trp Ala Phe Pro Glu Asn Lys Leu Gly Ser Arg Ile Ile
    290                 295                 300

Ala Thr Thr Arg Arg Ile Asp Val Ala Glu Tyr Val Gly Gly Cys Tyr
305                 310                 315                 320

Met Met Lys Pro Leu Thr Arg Glu Lys Ser Asn Ile Leu Phe Tyr Gly
                325                 330                 335

Arg Ile Phe Gly Ser Glu Gly Lys Cys Pro Pro Glu Leu Ser Asp Ala
        340                 345                 350

Ser Glu Lys Ile Leu Asn Lys Cys Gly Gly Val Pro Leu Ala Ile Ile
    355                 360                 365

Thr Thr Ser Ser Leu Leu Ala Ser Lys Ser Arg Asn Ile Lys Glu Trp
    370                 375                 380

Tyr Asn Val Ala Asp Ser Ile Gly Ser Arg Ile Leu Lys Asn Ser Thr
385                 390                 395                 400

Glu Met Glu Asn Leu Arg Asn Ile Leu Leu Leu Ser Tyr Tyr Asp Leu
                405                 410                 415
```

```
Pro Ala Arg Leu Lys Thr Cys Leu Leu Tyr Leu Ser Ile Phe Pro Glu
            420                 425                 430

Asp Cys Glu Ile Gly Met His Arg Leu Ile Trp Arg Trp Ile Ala Glu
            435                 440                 445

Gly Phe Phe Asn Gly Glu Leu Ala His Asp Gly Leu Phe Asn Leu Gly
            450                 455                 460

Glu Ser Cys Phe His Glu Leu Ile Arg Arg Ser Met Val Gln Pro Val
465                 470                 475                 480

Thr Leu Glu Gly Thr Gly Leu Val Tyr Ala Cys Arg Val His Asn Met
                485                 490                 495

Phe His Asp Leu Ile Leu Tyr Met Ser His Glu Glu Phe Val Ser
            500                 505                 510

Ala Val Asn Glu Lys Phe Gly Leu Leu Asp Val Arg Ser Arg Arg Leu
            515                 520                 525

Ala Phe Gln Asn Ile Thr Lys Glu Gln Tyr Arg Leu Val Glu His Pro
            530                 535                 540

Arg Leu Ala Gln Leu Arg Ser Leu Asn Ala Ile Gly Cys Pro Ile Tyr
545                 550                 555                 560

Ala Ile Pro Pro Ile Glu Ser Tyr Lys Leu Leu Arg Val Leu Asp Phe
                565                 570                 575

Glu Asn Cys Ala Gly Ile Glu Gly His Asp Leu Val His Leu Gly Lys
            580                 585                 590

Leu His His Leu Lys Phe Leu Gly Leu Arg Asn Thr Phe Ile Gly Lys
            595                 600                 605

Leu Pro Glu Gly Ile Gly Asn Leu Lys Phe Leu Gln Thr Leu Asp Leu
610                 615                 620

Asp Gly Thr Gly Val Glu Glu Leu Pro Gln Ala Leu His Asn Leu Thr
625                 630                 635                 640

Glu Leu Met Cys Leu Ile Ala Asp Trp Arg Thr Arg Val Pro Asn Trp
            645                 650                 655

Ile Gly Asn Leu Thr Ser Leu Gln His Leu Val Ile Tyr Pro Gly Gly
            660                 665                 670

His Asp Asp Glu Asp Ser Ala Ser Arg Phe Val Asn Glu Leu Gly Lys
            675                 680                 685

Leu Arg Gln Leu Arg Val Leu Arg Phe Leu Ile Lys Ala Gln Asp Glu
            690                 695                 700

Gly Gln Leu Arg Asp Leu Leu Glu Ser Leu Ser Asn Leu Pro Glu Ile
705                 710                 715                 720

Glu Ala Ile His Phe Asp Tyr Tyr Gly Val Gln Leu Asn Arg Gly Val
                725                 730                 735

Gln Leu Glu Pro Glu Gly Tyr Ala Leu Ser Arg His Ile Arg Ser Met
            740                 745                 750

Glu Leu Arg Trp Leu Glu Phe Ser Arg Leu Pro Leu Trp Ile Asn Pro
            755                 760                 765

Gly Gln Leu Pro Asn Leu Tyr His Leu Trp Leu Met Val Ser Asp Ala
            770                 775                 780

Glu Glu Arg Asp Leu Glu Ile Leu Gly Gly Phe Pro Val Leu His Ser
785                 790                 795                 800

Leu His Leu Leu Ile Val Asn Thr Glu Arg Glu Asp Val Met Thr Cys
                805                 810                 815

Gly Cys Gly Gly Phe Lys Asn Leu Lys Cys Cys Ser Ile Thr Lys Pro
            820                 825                 830

Leu Lys Phe Val His Gly Ala Met Pro Arg Leu Glu Val Leu Asp Phe
```

-continued

```
              835                840                845
His Phe Ser Val Gln Leu Leu Thr Asp Ser Asn Gln Glu Phe Asp Phe
    850                855                860

Asp Phe Gly Leu Gly Asn Leu His Trp Leu Gln Gln Ala Ile Val Gln
865                870                875                880

Ile Thr Ala Leu Gly Glu Val Glu Ser Val Gly Arg Ala Gln Val
                885                890                895

Ala Leu Arg Asp Ala Ile Arg Thr His Pro Asn Arg Pro Thr Leu Glu
                900                905                910

Ile Asn Leu Phe Gly Gln Thr Ile Pro Pro Glu Leu Pro Lys Gln Asp
                915                920                925

Asp Asp Gly Ala Lys Ile Val Glu Ile Ser Pro Ala Glu Ser Ser Arg
    930                935                940

Gln Ala Gln Glu Arg Glu Lys Arg Ser Ile Asp Val Ala Thr Lys Lys
945                950                955                960

Ala Thr Arg Val Pro Ser Phe Tyr Thr Lys Ser Ser Ile Asp Glu Pro
                965                970                975

Met Asp Gln Leu Ile Asn Met Leu Ser Val Val Asp Asp Glu Ala Tyr
                980                985                990

Thr Lys Asn Ile Lys Ile Leu Ser  Ile Val Arg Ser Glu  Gly Leu Gly
                995                1000                1005

Lys Thr Thr Leu Ala Gln Lys  Ala Phe Glu Glu Leu  His Ser Gln
    1010               1015                1020

Phe Asp Arg Gly Ala Phe Val  Leu Leu Gly Gln Asn  Pro Asp Leu
    1025               1030                1035

Arg Arg Val Phe Ala Asp Ile  Leu Arg Gly Leu Asp  Lys Gln Arg
    1040               1045                1050

Tyr Ile Asp Phe Pro Val Ala  Ile Leu Asp Leu Val  Asp Leu Ile
    1055               1060                1065

Trp Leu Val Arg Lys Ser Leu  Ile Asn Lys Arg Phe  Phe Ile Val
    1070               1075                1080

Phe Asp Asp Ile Cys Asp Val  Lys Ala Trp Glu Ile  Ile Lys Cys
    1085               1090                1095

Ala Leu Ile Glu Asn Asn Asn  His Ser Val Val Leu  Thr Thr Ser
    1100               1105                1110

Arg Asn Thr Gly Ile Thr Glu  Ile Ile Gly Gly Ser  Lys Gln Leu
    1115               1120                1125

Gln Pro Leu Ser Ala Thr Ile  Ser Lys Asn Leu Leu  Cys Lys Arg
    1130               1135                1140

Leu Phe Gly Ser Ala Gly Lys  Cys Pro Ser Glu Leu  Val Asn Ile
    1145               1150                1155

Cys Asp Asn Leu Val Glu Glu  Cys Gly Gly Ile Leu  Ser Val Ile
    1160               1165                1170

Asp Glu Thr Val Thr Leu Leu  Ala Ser Ile Pro Pro  Thr Val Glu
    1175               1180                1185

Asn Trp Glu Ala Val Tyr Ala  Arg Arg Met Leu Asp  Arg Ser Tyr
    1190               1195                1200

Pro Gly Leu Thr Asp Ser Leu  Lys Asn Cys Leu Leu  Tyr Phe Thr
    1205               1210                1215

Met Phe Arg Arg Gly His Glu  Ile Ser Gly Glu His  Leu Ile Cys
    1220               1225                1230

Ala Trp Ile Ala Glu Gly Phe  Val His Gly Gln Glu  Val Ala Glu
    1235               1240                1245
```

```
Thr Tyr Leu Ser Asp Leu Val Lys Lys Leu Ile Asp Ala Val
    1250            1255            1260

Glu Val Asp Ala Gly Gly Lys Val Leu Thr Cys Arg Met Tyr Asp
1265            1270            1275

Leu Val His Asp Phe Ile Val Ser Lys Ser Ile Glu Glu Arg Phe
    1280            1285            1290

Val Tyr Ile Leu Asn Asp Ser Glu Gly Arg Asp Leu Ser Glu Ala
    1295            1300            1305

Val His Val His Gln Arg Leu Tyr Ile Gln Gly His Asn Asn Lys
    1310            1315            1320

Glu Leu Asp Leu Gln Ile Pro Trp Leu Pro Gln Val Lys Ser Leu
    1325            1330            1335

Val Ser Cys Gly Thr Ala Pro Ser Ile Leu Lys Phe Lys Gly Leu
    1340            1345            1350

His Val Met Asp Leu Gly Ala Cys Glu Ser Leu Gln Ala Ser His
    1355            1360            1365

Leu Lys Gly Ile Asn Asn Val Ser Ser Leu Arg Tyr Leu Val Ile
    1370            1375            1380

Gly Gly Lys Cys Ile Ser Gly Ile Pro Lys Glu Ile Ala Lys Leu
    1385            1390            1395

Glu His Leu Arg Thr Leu Asp Leu Ser Ala Ser Gly Leu Asn Glu
    1400            1405            1410

Leu Pro Glu Tyr Val Phe Met Ile Arg Lys Leu Glu Arg Leu Ile
    1415            1420            1425

Val Asn Ser Gln Met Lys Ile Ser Tyr Gly Ile Ala Lys Met Ser
    1430            1435            1440

Ala Leu Gln Glu Leu Gly Asp Ile Asn Val Thr Asp Pro Glu Leu
    1445            1450            1455

Leu Lys Ser Leu Cys Lys Leu Thr Lys Leu Arg Val Leu Arg Ile
    1460            1465            1470

Ser Ile Trp Ser Trp Asp Asp Ser Leu Lys Asn Tyr Phe Lys Gln
    1475            1480            1485

Leu Cys Asp Asn Leu Arg Ser Leu Val Gln Cys Thr Glu Asn Ile
    1490            1495            1500

Gln Ser Leu Ser Ile Met Thr Cys Cys Ser Leu Val Phe Met Asp
1505            1510            1515

Asp Leu Gly Glu Asn Trp Thr Pro Gln Cys Leu Gln Lys Leu Glu
1520            1525            1530

Val Gly Cys Ser Ala Phe Asp Ile Leu Pro Ser Trp Phe Gly Ser
    1535            1540            1545

Leu Ser Ser Ile Ser Thr Leu Thr Ile Glu Val Tyr Lys Leu Ser
    1550            1555            1560

Gln Asp Ile Ile Asp Thr Leu Gly Arg Leu Ala Gly Leu Gly Ser
    1565            1570            1575

Leu Ser Leu Thr Ser Lys Gln Val Pro Lys Gly Tyr Phe Val Ile
    1580            1585            1590

Gly Ser Asp Arg Phe Asn Lys Leu Gln Ser Leu Lys Phe Val Ser
    1595            1600            1605

Asn Ala Met Val Glu Met Phe Pro Arg Gln Gln Ser Asn Gly Thr
    1610            1615            1620

Glu Gln Leu Lys Arg Leu Met Ile Val Phe His Ala Ser Arg Thr
    1625            1630            1635
```

```
Gln Asp Val Asn Lys Asp Phe Cys Phe Gly Leu Glu Asn Leu Ser
    1640                1645                1650

Ser Leu Glu His Val Arg Val Glu Ile Ile Cys Phe Asp Ala Ser
    1655                1660                1665

His Asn Met Val Lys Asn Ala Glu Ala Ala Val Gln Lys Ala Ile
    1670                1675                1680

Ser Gly Thr Ser Ile Ala Asn Leu Glu Ile Arg Arg Leu Gln Glu
    1685                1690                1695

Asn Ser Met Thr Gln Asp Glu Ala Asp Leu Cys Asp Ala Val Gln
    1700                1705                1710

Glu Gln Asn Asn Gln Lys His Gln Lys Met Lys Arg Ile Tyr Ala
    1715                1720                1725

Thr Gly Asp Trp Gln Leu Glu Ile Ala His Ser Ser Met Glu Ser
    1730                1735                1740

Gln Asp Gly Tyr Leu Thr Ser Leu Pro Asn Gln Glu Ser Ala Asp
    1745                1750                1755

Val Val Gly Ser Asp Ser Ile Val Glu Pro Leu Val Asn Glu Met
    1760                1765                1770

Asn Ser Gln Thr Ile Lys Arg Asp Gln Ser Thr Asn Phe Ser Glu
    1775                1780                1785

Asp Glu Asp Leu Met Leu Val Ser Ser Tyr Leu Asn Val Ser Lys
    1790                1795                1800

Asp Ser Ile Thr Gly Arg Asp Lys Lys Glu Gly Thr Phe Trp Glu
    1805                1810                1815

Arg Val Trp Glu Tyr Tyr Asn Lys Asn Arg Thr Phe Glu Ser Asp
    1820                1825                1830

His Ser Trp Ser Ser Leu Lys His Arg Trp Leu Ala Ile Gln Lys
    1835                1840                1845

Glu Val Asn Ile Phe Gln Gly Tyr Tyr Asp Ala Ile Glu Arg Lys
    1850                1855                1860

Asn Gln Ser Gly Gln Thr Ser Asp Asp Lys His Ala Glu Ala Glu
    1865                1870                1875

Val Glu Phe Arg Glu Lys Gln Gly Lys Ala Phe Ser Val Phe His
    1880                1885                1890

Val Trp Met Ile Leu Arg His Glu Pro Lys Trp Ala Phe Arg Glu
    1895                1900                1905

Ser Lys Ile Lys Asp Gln His Glu Ala Asn Asn Ala Asn Thr Asp
    1910                1915                1920

Ala Pro Ala Asn Ile Tyr Arg Pro Gln Gly Arg Lys Ala Glu Lys
    1925                1930                1935

Glu Lys Ala Arg Ala Arg Lys His Gly Gly Ser Asp Val Asp Gly
    1940                1945                1950

Asp Pro Phe Ile Glu Glu Val Lys Asn Met Arg Glu Ala Arg Glu
    1955                1960                1965

Glu Thr Glu Arg Asp Arg Lys Thr His Asp Asp Lys Phe Tyr Glu
    1970                1975                1980

Leu Glu Lys Ser Lys Leu Glu Leu Glu Arg Asp Arg His Asp Lys
    1985                1990                1995

Glu Ile Met Gln Thr Asp Thr Ser Thr Met Asp Glu Glu Ser Lys
    2000                2005                2010

Gln Tyr Phe Lys Leu Met Lys Gln Glu Ile Leu Ala Arg Arg Phe
    2015                2020                2025

Gly Ser Ser Gln Pro
```

<210> SEQ ID NO 3
<211> LENGTH: 7821
<212> TYPE: DNA
<213> ORGANISM: Zea mays

<400> SEQUENCE: 3

```
atggagttcg caactggagc gctaggcacc cttcttctca agctctccat gctgcttcat      60
ggtgagtaca acctggagaa gggcgtcagg ggggacatcc agcgcgtcat gaacaagctc     120
gagcgggttc attctgtcct cggccatgtt gtcgaagtgc ctgtgccact gaagccacgt     180
cctgatctgg tcagaatgtt ggcacgcagc gtcagggagc tatcctacga catggaggac     240
ttcgtcgaca ccttcctggt gcgtgtccaa ggccctgaac gcaccagcaa agaagcgcc      300
aaaatattca tgaataagac atatatggtc gtgaatcgcc atgagatcgc ccagaccatc     360
aaggacttcg aagagcgcgt ccagcagata gatgagcgtc gtcaaaggtc attgaaacac     420
ttaatttcca ctttggcttg cgtgcatatg aactttcacc tttactgtct ttcttccatt     480
ttatttcctt ttctggttct aacaggtacg atgttgatgc tatggttccc cgtgtcaaaa     540
ccttggttga tcctcgcata tttgctctga agtacaccaa ggccacggac cttgtcggca     600
tggatgaggc aagggaggaa ctaatcacaa ggttgaccaa ggaagatgac acctccactg     660
aacaaaggcg agtctctatc gttggttttg gaggacttgg caagacagcg cttgcaaaag     720
cagtttatga caaacttaaa gctaaggggg aattccattg cgcggccttt gtgtcggtgt     780
ctcggtttcc tcagctcgaa aaattcttca aggaattgct tatgagctt gacgagactg      840
agtacaagga acttattgac atcagcaccc cattggaact tatgaatcta gtgcatgaat     900
tccttcataa taagaggtac acgcgtacat gtaccacacc tagtgtgcat tatatgttca     960
ttccacggaa atatccatat tatagagtaa tatgcttata tatattattg caattcatat    1020
ctttagctat gcttacatta cttctccaat taatacaata aatataggta ccttattgct    1080
gtcgatgaca tatgggatac tgacgcatgg gcaatgatac aatgggcttt tcctgagaat    1140
aagctaggaa gcagaataat cgcaactact cgcagaattg atgttgctga gtatgtaggt    1200
ggttgctata tgatgaaacc tcttactcga gagaaatcaa atatattatt ctatggacga    1260
atatttggct ctgaaggtaa atgtcctcct gaactttctg atgcgtctga gaaaatattg    1320
aataaatgcg gaggcgtgcc attggctatt attactacat ctagcttgct ggctagtaag    1380
tcaagaaaca taaagaatg gtacaatgtt gctgattcta ttggttccag aatactaaaa     1440
aacagtactg aaatggagaa tttgaggaac atactgctgc ttagctatta tgatctacca    1500
gcacgattaa agacatgttt gttatatctg agtattttcc ctgaagattg tgagattggg    1560
atgcatcggt taatatggag gtggatagct gaaggttttt tcaatggaga actagcacat    1620
gatgggctct ttaaccttgg cgaatcttgt ttccacgagc tcataagaag aagcatggtg    1680
cagccagtaa cacttgaagg cacgggtctt gtatatgctt gtcgtgttca taatatgttt    1740
catgatttga tcctctacat gtcacacgaa gaagaatttg tttctgcagt caatgaaaag    1800
tttggtcttc tagatgttcg ttctcggcgg ttagcattcc agaacataac aaaagagcag    1860
tacagacttg tggaacatcc acggctggca caattgaggt cacttaatgc cattggatgt    1920
cctatatacg cgataccticc aattgaaagc tataaattat tgcgtgtact ggatttcgaa    1980
aattgtgcag gtattgaagg ccatgatctt gttcatcttg ggaaattgca tcacctcaag    2040
ttccttgggc taagaaacac gtttatcggt aagctgccgg aaggaatagg gaacctcaag    2100
```

```
tttctgcaaa cattggacct cgatggaact ggtgtggaag aattacctca agccttgcat   2160
aatcttacag aattgatgtg cctaattgct gactggagaa cgagagtgcc caattggatt   2220
ggtaacctca cgtccctgca gcacttggtg atttatcctg gtgggcatga cgatgaggat   2280
tctgcgagca ggtttgttaa tgagctggga aagctgagac aactaagggt gctccgtttt   2340
ttgataaaag cacaagatga agggcagctg agagatttgc tagagtccct atcgaatctg   2400
ccagagatcg aggctataca ttttgattac tatggagtac agttaaatag aggtgttcag   2460
ttggaacctg aaggctatgc cctctctaga catattcgtt ccatggaatt gcgctggttg   2520
gagttctcaa ggctgcctct ttggattaat cctggacaac ttcctaacct ctaccactta   2580
tggctgatgg tatctgatgc ggaagagcgg atctggaaaa tccttggggg gtttccagtg   2640
cttcactccc tccacttgtt gattgtgaat actgaacgtg aagatgtcat gacttgtggc   2700
tgtggtggat tcaagaattt gaaatgctgc agtataacta aaccgctgaa atttgtacat   2760
ggagctatgc ccaggcttga agtcctcgat ttccatttca gtgtgcaact cctaacggat   2820
tcaaaccaag aatttgattt tgactttggc ttgggaaacc tacattggct tcagcaagcc   2880
atcgttcaaa tcacagccct tggtgaggag gtggagtctg tggggagagc acaggtggct   2940
ctgcgggatg caatacgtac ccatcccaac cgtcctaccc ttgaaataaa cttatttggg   3000
caaacaatac ctccagagtt accaaaggtc aggactcttt gtcatctctc tctcacctca   3060
tttcgttgtc ttgttttcat ttgccttatt tcactgtttc agcaagacga cgatggagcg   3120
aaaattgtgg agatatcacc ggccgagagt agtcgtcaag ctcaagagcg ggagaaaaga   3180
agcatcgatg tggcgacgaa gaaagcaaca cgggtgccgt cttttttacac aaagtcatca   3240 attgatgagc caatggatca gctcataaac atgctatctg tggttgatga cgaagcctac   3300
actaagaaca taaagatact atctattgta aggtctgagg gactggggaa gactactctg   3360
gcccaaaaag cattcgaaga gctccattcg caatttgacc gtggggcgtt cgttctacta   3420
ggccagaatc ctgacttgag gagagtcttt gctgacattc tccgtggtct tgacaagcaa   3480
aggtacatag atttcccagt ggcaatattg gatctagtgg acctgatctg gctagtccgt   3540
aaatcgctca taaacaaaag gtatgtccaa cccactgaca tgctagtagc ctagtactac   3600
ctttattcag ctatatattt gctcaatata ttgtctccgt tcttttttttt tatttgacgt   3660 ggttgattat tttttcttca aaattctaat cactcgtgta ctaaaaaaaa tctgtgtgtt   3720
atatccatga gtgttatttc gacactgccg gttaaaccgg tgagtattga tttctctgat   3780
tttgctttgt ttgacttggt tcttcttggt gtcttcagca tttcatccca tagacctata   3840
aacctgagaa tatacatcta gaaaacattg ttaatctaag tgttgtgtgt caatcaatca   3900
ccaaaacgaa gcaccgaaat atgacataag agaccatttt tgctacagtt gttgtcagta   3960
gtagttacta ctaaatatgg attataaccc ttggatacta ttatttttcc aggttcttta   4020
ttgtatttga tgatatatgt gatgtaaaag catgggaaat tataaagtgc gctttgattg   4080
aaaataacaa ccacagtgta gttcttacga caagtcgcaa cactggtatt actgaaatta   4140
ttggtggcag caagcaatta caacctctat cagcaactat ctctaaaaat ctactctgca   4200
aaaggttatt tggatcggca ggcaagtgtc cttctgaact agtaaatata tgtgacaatc   4260
ttgtagaaga atgtggtgga atactatctg tgatcgacga aactgtgaca ttgcttgcaa   4320
gtataccacc aacagtggag aactgggagg cagtgtacgc cagaagaatg ttggatcggt   4380
cttatcctgg tttaactgac agtctaaaga attgcttact ctattttact atgtttcgaa   4440
```

```
gaggacatga gattagtgga gaacacttaa tatgtgcatg gatagctgaa ggttttgtac    4500
atgggcaaga ggtagcagag acctacctta gtgatctagt aaaaaagaaa ttaatcgatg    4560
cagtggaggt tgatgctgga ggaaaggtcc tcacgtgccg catgtatgac ttggtgcatg    4620
actttatcgt ctcaaaatca attgaagaac gatttgttta tattttaaat gactcggaag    4680
gcagagattt gtcagaagca gttcacgttc accagcgact atacatccag ggacataata    4740
acaaagaact agacctgcaa attccttggc tgccccaagt gaagtcactt gtctcctgtg    4800
gtactgcgcc atccatctta aagtttaagg gtctacatgt tatggattta ggggcctgtg    4860
aatctttgca ggctagtcat ctcaagggta taaataatgt aagttctttg agatatctgg    4920
tcataggagg taagtgtatc tctggcatcc ctaaggaaat tgcgaagctg aacatttgc     4980 ggacactaga tttaagtgca agtggtctaa atgaattgcc agaatatgtt ttcatgataa    5040
gaaaattgga acgcctaatt gttaatagtc agatgaagat atcatatggt attgcaaaga    5100
tgtctgcttt acaggagcta ggcgatatca atgtcaccga cccagagttg ctgaaaagtc    5160
tctgtaagct aaccaaattg agggttctta gaatttccat atggtcatgg gatgatagtt    5220
tgaagaacta ttttaaacaa ctgtgtgaca acttgcgttc actggttcag tgcacggaga    5280
acatccagag tctctccata atgacatgct gctccctggt tttcatggat gatttgggtg    5340
agaattggac ccctcaatgt ctccagaagc tcgaggtcgg ttgcagcgca tttgacatat    5400
tgccaagttg gtttggctca ctttctagta tctccacgtt aacaatcgag gtctacaagc    5460
tgtcacagga cataattgat acgctcggaa ggctggctgg tcttggttct ctatccctga    5520
catcgaaaca agtaccaaaa ggatactttg tgatcggctc tgacaggttc aataagctac    5580
agagcttaaa gtttgtgagc aatgcaatgg tagagatgtt tccacgtcaa caatcaaatg    5640
gcacggaaca gctcaaaagg cttatgattg tgttccatgc ttcacgtaca caagatgtga    5700
acaaagattt ctgctttggt ttggagaacc tgtcttccct agagcatgtt cgtgttgaaa    5760
taatttgttt cgatgccagc cataacatgg tgaaaaacgc agaagctgca gttcagaaag    5820
ctatatctgg cacaagtatc gcaaatctgg aaatacgaag acttcaggaa aatagtatga    5880
cacaggacga agcggacctc tgtgatgcag tacaagagca gaataatcag aagcaccaga    5940
aaatgaagag gtactaattt tccactccta caatacaacg atgtcaaata aaattatttc    6000
tcttgtattt tcttataaag ttcggcccct gagagcatct ccaagagagg tcttaaacta    6060
ggtcctatct tcaaatatag gacataagag taaaacatgg ctttgagatg gatcgataga    6120
atctcagcag caacaggtaa agagttatag taggccttcg ttaaatgtcg ccatggatgt    6180
gattcgcaag attctggagg ttcaatgtct gctagagctg cttcatgccc acaaccccaa    6240
tttcgaacga actcaatctt aggcaacaac gatccctctg ggatgtccga ttttaggtag    6300
tattctttcg aatttaacga tatgctgcag aaaggcattt tagatcccac gtagctaggc    6360
gcccaggcat agccgaacag acccaaactc gcgttcggac gctcagttat gcagtcatgc    6420
taggtctcat cactgatgat gtaatgcaga atttatgcaa cggggactg gcaactggaa     6480 atagcacata ggtctgtaga atcagatgag tagctgaaag gttaatattc tgaatttcag    6540
agttattact aatatatggc tattggtgta ctattctacc tactgtcact aattgaaatg    6600
tctcttgtta tacctatgtg tgatgatgta tttgtgaaac attccatatg cccgacataa    6660
aatcattgat attgtttatg ggattattgt taagatggat gtatgattat tggcattgag    6720
ttgtttcaac tagcccttca tcgctagcta catttctcat ggatgcttgt ttgaatagta    6780
cttgcaatat gcttcaacta gatggaatgc tcggatactg atatgctact atgtattcct    6840
```

-continued

```
attttgcagt tctatggagt cccaggatgg gtacctcact tctttaccga accaggaaag    6900
tgcagatgtt gttggctccg atagtattgt ggaaccacta gtgaatgaaa tgaactcgca    6960
gacaattaag agggatcaat ccacgaattt cagtgaagat gaggacttaa tgttggtttc    7020
tagctacctt aatgtaagca aagattctat tactggaagg gataaaaaag aaggcacatt    7080
ttgggaaaga gtatgggaat actataacaa gaataggaca ttcgagtccg atcatagttg    7140
gtcgtcattg aaacatcgct ggcttgcaat tcagaaggaa gtgaatatct ttcaaggtta    7200
ctatgatgcc atagaaagga aaaatcaaag tggccagaca agtgatgaca aggtgaatca    7260
tacattttgt accattattt atacttctta acataacatg caacttctca catttgtgaa    7320
tcctgtgttg ttttgtagca tgctgaagca aagtagaat tccgagaaaa acaagggaag    7380 gcttttctg tattccatgt gtggatgatt ctaaggcatg agccaaagtg ggcatttaga    7440
gaatcaaaga tcaaagacca gcatgaagca acaatgctaa atactgatgc tcctgccaac    7500
atttatagac acaggggag gaaagctgag aaggaaaagg ctcgtgcgag aaagcatggt    7560
ggatctgatg ttgatggtga tccgttcatc gaagaagtaa aaaatatgag ggaagcacgg    7620
gaagaaacag aacgagaccg aaagacccat gatgacaagt tctatgagtt ggaaaagagt    7680
aagcttgaat tggagcgaga tcgacatgac aaagagataa tgcaaacaga cacaagcaca    7740
atggatgaag aatcgaaaca atacttcaag ttgatgaaac aagagatttt ggctcgccgt    7800
ttcgggagta gtcagccata g                                              7821
```

```
<210> SEQ ID NO 4
<211> LENGTH: 12662
<212> TYPE: DNA
<213> ORGANISM: Zea mays

<400> SEQUENCE: 4
atttaatgag acctgtccat tccgcaggcg gcgtgcctgt ccattccact ggcaggcgat     60
gtgctacctc cgcatttaat gagacctgtc cattccgctg gcaggcagcg acctgtccat    120
cccacaggcg gcatgcatgt ccgttccatt ggcagactgc atgcccatac cgccgcgtgc    180
actacgccca tcattactcg tatgttacca aggaagctgc cactgcatgt caacactgcg    240
cgtactgcgg acaacatggg cctggagatt gcacagacgt cacctgcatt agttgctcta    300
ggtattccat tcattatgtt cctgggccca catgttgggg ctcagcaccc ttgtatgtgc    360
ctcccttgag ctataaaagg gaaggcacac aacgttacaa ggcaagctct caagtcactc    420
agacttactt agaccctcga gaagttctcc aagctctcga gtatcagcaa tactacatag    480
tggagaaggg ttttacgctc cggtggcctg aaccactcta aactcttgtg tgctctcgtg    540
ctttcatcga ccatctagca gacaggcaaa acgcttaggc ccctcctca tcttaggatt    600 tagggcgggt gcgttccgcc acccggctag agatttcctc tccgacactc acatacttcc    660
acgtcttgct cacaaatgct cgacaagacc attttgtagt gtgcaagacc tttcctagcg    720
acgaagattg aagtgattaa tcacccaatc cgagtgtcct tcaatgagtt ggcacggttc    780
aaatgcagaa ctactctctc cgaaattggt atttgctgca aagtcgcctt cgtcttcgac    840
aatcatgtta tgcattatta tgcatgcagt tattatctca gtaagacagt tgcaatccca    900
accgtacgca ggatcacgta gcaccaccca gcgtgcttga agaactccaa atgggcactc    960
aatatccttc ctgtaacttt cctacatttg tctgaaatat atcttttttt cctcataagg   1020
gtgtctaatg gctttcacaa aagttggcca gttcagatat atgccattag ctaggtaata   1080
```

-continued

```
accaaagttg tatgcatgat cgttgattat gtaatgaatg ggtggcattc gaccgcttgt     1140
catagggtca ataccggcg atcaatgtag cacgttcacg tcattgtttg ttctaggcat      1200
gccaaaaaaa agtatgccaa atctagagat cgtacgttgc gacagcctcg agtatcatgg    1260
taggtcttaa atttcgacca cagaactatc ctcgccacgc ggttggacag ttcctccact    1320
cccaatgcat gcaatctatg aacccaaca ttcctggaaa cccctcgac tcgctattgt      1380 gcatgatgcg tgcaatgtct gcttcattag gagttcgtag ataccaccca ctaaaatatg    1440
caattaatgc acgatagaaa tgaataaggc attccctaac ggtagactcc cctatttgaa    1500
tgtactcgtc tacgacatca gtaggtaaga tgtaagcaag gatccgcatt gctgcacata    1560 cttttttgaag tggttcgagt ccagctaggc cagtagcgtc gacccgttga gtaaagtaac   1620
tatcctgctg ttgcagtcct tccataatgc ggaggaacaa tgaactactc atgcggaacc    1680
tataaaatgt aataggtaaa gtatgaaaga cactgttaat gcaaaactta ataatacaag    1740
tatgtagttg ttaccttctg cgaaacacgt ggggtggata cacgagattt agccgaagta    1800
gtgatggtgg atgagattct ctccagcata atgatccctg tgaatcacgc ggcggggat     1860 accggaacgt ctacacctac ggtgtgtagc cttaatggtg agggtaagaa gagtggcaag    1920
cataagtgtg ttgtcgtcac tatcactcga atcggaatca tcgtccctac gcaaagacga    1980
cacaacgtac aaagtcttgt tagcttgagt tgaggagtga gatgtgcaca caatgggaa     2040 gagcacgtac ccatatgtat agacgagatg gagttagctt tgttgcaag ctcgtgtctt     2100 gcactgaaag cctcatgtgt cttgctgtgt atggttgtcg catgggtgct tgcaatggaa    2160
tttggtcgaa tattcatgtc atatttcaat cgtgctgaaa tattgggtgc caacagattc    2220
ataatgcatt ggaagggagg cttgcagtgt acggttgttg cgtatgtgct tgcgaaggaa    2280
aagcttcgaa cgataatgca gatcaactat gagcatgggt atggtccaat aacatcgatg    2340
gtaattacaa aacgaaaaat aattacttcg ttgttggtaa tggtatatga tgaatacgaa    2400
tttaataaat attcaccaga aatatgtacg acacaatata tttaattatg agtttttaa     2460 aatttagaaa ttaaataata ggtaattata cgtattatgt gtcccacaat aacttataga    2520
gattatatgt ctaattgaaa aattaattca attattcaat ggatttatac gttaagaaaa    2580
taaaaattga aaaaatatgg tagttaatga tagttggatt gatatatata tattttatgc    2640
gtagaggata tataaaggaa tatatagacg gaatagttac agaaagattg aatatagtgg    2700
agtgaatttt gctgtgctac gtagtaatat ataacgcgaa aaatttaggg aaacgctgag    2760
ggctgcagat acagctggcc atgctatcaa tagattagta cttggttgcc acttgccagt    2820
agccgcactt tcctcgatat gcccaagcga gagagagaga ttcctaagtt gattcttctg    2880
tggatgaaga tgaaatctac ttctgaaatc ttgccaaccg tccaactctg tttgatctaa    2940
tttctatatc ctccggccac caagttcgtg tcaaataagc gagcacagct aggtaagtag    3000
ctgattcgaa ttccaacaaa acatctcatc cctttagtc tcttgtgcta gatcttatgc      3060
gtctgcaacc ttgggagcta gctagccatg gagttcgcaa ctggagcgct aggcacccctt   3120 cttcccaagc tctccatgcc caagcgagcg agagagagag agattcctta gttgattctt    3180
ctgtggatga agatgaaatc tacttctgaa atcttgccac cgtccaactc tgtttgatct    3240
aatctctata tcctccggcc accaagttcg tgtcaaataa gcgagcacag ctaggtaagc    3300
agctgattcg aattccaaca aaacattgta tcccttttag gccgtgtttg ttttggcttc    3360
tggcagcttc tggtcattaa aagctgctgc aaactgtcaa acgcttagct tttcagccag    3420
tttctataaa attcgttgag gcaaaaatca tccaaaatca acataaacac ataaccggtt    3480
```

```
gagtcgttgt aataatagga atccgtcact ttctagatcc tgagtcatat gaacaacttt    3540
atcttcgttc acacgtaatc gtattgatac tcagcttctc actacagaca gattctcctc    3600
ataatcagat tttcaaaaaa actgaataga aaaagctaa accaaacgtg ccttagtctg     3660
ttgcgctaga tctcatgcgt ctgcaacctt gggagctagc tagccatgga gttcgcaact    3720
ggagcgctag gcacccttct tctcaagctc tccatgctgc ttcatggtga gtacaacctg    3780
gagaagggcg tcaggggga catccagcgc gtcatgaaca agctcgagcg ggttcattct     3840
gtcctcggcc atgttgtcga agtgcctgtg ccactgaagc cacgtcctga tctggtcaga    3900
atgttggcac gcagcgtcag ggagctatcc tacgacatgg aggacttcgt cgacaccttc    3960
ctggtgcgtg tccaaggccc tgaacgcacc agcaaaagaa gcgccaaaat attcatgaat    4020
aagacatata tggtcgtgaa tcgccatgag atcgcccaga ccatcaagga cttcgaagag    4080
cgcgtccagc agatagatga gcgtcgtcaa aggtcattga acacttaat ttccactttg     4140 gcttgcgtgc atatgaactt tcacctttac tgtctttctt ccattttatt tcctttctg     4200 gttctaacag gtacgatgtt gatgctatgg ttccccgtgt caaaaccttg gttgatcctc    4260
gcatatttgc tctgaagtac accaaggcca cggaccttgt cggcatggat gaggcaaggg    4320
aggaactaat cacaaggttg accaaggaag atgacacctc cactgaacaa aggcgagtct    4380
ctatcgttgg ttttggagga cttggcaaga cagcgcttgc aaaagcagtt tatgacaaac    4440
ttaaagctaa aggggaattc cattgcgcgg cctttgtgtc ggtgtctcgg tttcctcagc    4500
tcgaaaaatt cttcaaggaa ttgctttatg agcttgacga gactgagtac aaggaactta    4560
ttgacatcag caccccattg gaacttatga atctagtgca tgaattcctt cataataaga    4620
ggtacacgcg tacatgtacc acacctagtg tgcattatat gttcattcca cggaaatatc    4680
catattatag agtaatatgc ttatatatat tattgcaatt catatcttta gctatgctta    4740
cattacttct ccaattaata caataaatat aggtaccta ttgctgtcga tgacatatgg     4800
gatactgacg catgggcaat gatacaatgg gcttttcctg agaataagct aggaagcaga    4860
ataatcgcaa ctactcgcag aattgatgtt gctgagtatg taggtggttg ctatatgatg    4920
aaacctctta ctcgagagaa atcaaatata ttattctatg gacgaatatt tggctctgaa    4980
ggtaaatgtc ctcctgaact ttctgatgcg tctgagaaaa tattgaataa atgcggaggc    5040
gtgccattgg ctattattac tacatctagc ttgctggcta gtaagtcaag aaacataaaa    5100
gaatggtaca atgttgctga ttctattggt tccagaatac taaaaaacag tactgaaatg    5160
gagaatttga ggaacatact gctgcttagc tattatgatc taccagcacg attaaagaca    5220
tgtttgttat atctgagtat tttccctgaa gattgtgaga ttgggatgca tcggttaata    5280
tggaggtgga tagctgaagg tttttttcaat ggagaactag cacatgatgg gctctttaac    5340
cttggcgaat cttgtttcca cgagctcata agaagaagca tggtgcagcc agtaacactt    5400
gaaggcacgg tcttgtata tgcttgtcgt gttcataata tgtttcatga tttgatcctc    5460
tacatgtcac acgaagaaga atttgtttct gcagtcaatg aaaagtttgg tcttctagat    5520
gttcgttctc ggcggttagc attccagaac ataacaaaag agcagtacag acttgtggaa    5580
catccacggc tggcacaatt gaggtcactt aatgccattg gatgtcctat atacgcgata    5640
cctccaattg aaagctataa attattgcgt gtactggatt tcgaaaattg tgcaggtatt    5700
gaaggccatg atcttgttca tcttgggaaa ttgcatcacc tcaagttcct tgggctaaga    5760
aacacgttta tcggtaagct gccggaagga atagggaacc tcaagtttct gcaaacattg    5820
```

```
gacctcgatg gaactggtgt ggaagaatta cctcaagcct tgcataatct tacagaattg    5880
atgtgcctaa ttgctgactg gagaacgaga gtgcccaatt ggattggtaa cctcacgtcc    5940
ctgcagcact tggtgattta tcctggtggg catgacgatg aggattctgc gagcaggttt    6000
gttaatgagc tgggaaagct gagacaacta agggtgctcc gttttttgat aaaagcacaa    6060
gatgaagggc agctgagaga tttgctagag tccctatcga atctgccaga gatcgaggct    6120
atacattttg attactatgg agtacagtta aatagaggtg ttcagttgga acctgaaggc    6180
tatgccctct ctagacatat tcgttccatg gaattgcgct ggttggagtt ctcaaggctg    6240
cctctttgga ttaatcctgg acaacttcct aacctctacc acttatggct gatggtatct    6300
gatgcggaag agcgggatct ggaaatcctt gggggtttc cagtgcttca ctccctccac    6360
ttgttgattg tgaatactga acgtgaagat gtcatgactt gtggctgtgg tggattcaag    6420
aatttgaaat gctgcagtat aactaaaccg ctgaaatttg tacatggagc tatgcccagg    6480
cttgaagtcc tcgatttcca tttcagtgtg caactcctaa cggattcaaa ccaagaattt    6540
gattttgact ttggcttggg aaacctacat tggcttcagc aagccatcgt tcaaatcaca    6600
gcccttggtg aggaggtgga gtctgtgggg agagcacagg tggctctgcg ggatgcaata    6660
cgtacccatc ccaaccgtcc tacccttgaa ataaacttat ttgggcaaac aatacctcca    6720
gagttaccaa aggtcaggac tctttgtcat ctctctctca cctcatttcg ttgtcttgtt    6780
ttcatttgcc ttatttcact gtttcagcaa acgacgatg gagcgaaaat tgtggagata    6840
tcaccggccg agagtagtcg tcaagctcaa gagcgggaga aaagaagcat cgatgtggcg    6900
acgaagaaag caacacgggt gccgtctttt tacacaaagt catcaattga tgagccaatg    6960
gatcagctca taaacatgct atctgtggtt gatgacgaag cctacactaa gaacataaag    7020
atactatcta ttgtaaggtc tgagggactg gggaagacta ctctggccca aaaagcattc    7080
gaagagctcc attcgcaatt tgaccgtggg gcgttcgttc tactaggcca gaatcctgac    7140
ttgaggagag tctttgctga cattctccgt ggtcttgaca gcaaaggta catagatttc    7200
ccagtggcaa tattggatct agtggacctg atctggctag tccgtaaatc gctcataaac    7260
aaaaggtatg tccaacccac tgacatgcta gtagcctagt actaccttta ttcagctata    7320
tatttgctca atatattgtc tccgttcttt tttttattt gacgtggttg attatttttt    7380
cttcaaaatt ctaatcactc gtgtactaaa aaaatctgt gtgttatatc catgagtgtt    7440
atttcgacac tgccggttaa accggtgagt attgatttct ctgattttgc tttgtttgac    7500
ttggttcttc ttggtgtctt cagcatttca tcccatagac ctataaacct gagaatatac    7560
atctagaaaa cattgttaat ctaagtgttg tgtgtcaatc aatcaccaaa acgaagcacc    7620
gaaatatgac ataagagacc attttttgcta cagttgttgt cagtagtagt tactactaaa    7680
tatggattat aacccttgga tactattatt tttccaggtt ctttattgta tttgatgata    7740
tatgtgatgt aaaagcatgg gaaattataa agtgcgcttt gattgaaaat aacaaccaca    7800
gtgtagttct tacgacaagt cgcaacactg gtattactga aattattggt ggcagcaagc    7860
aattacaacc tctatcagca actatctcta aaaatctact ctgcaaaagg ttatttggat    7920
cggcaggcaa gtgtccttct gaactagtaa atatatgtga caatcttgta gaagaatgtg    7980
gtggaatact atctgtgatc gacgaaactg tgacattgct tgcaagtata ccaccaacag    8040
tggagaactg ggaggcagtg tacgccagaa gaatgtggga tcggtcttat cctggtttaa    8100
ctgacagtct aaagaattgc ttactctatt ttactatgtt tcgaagagga catgagatta    8160
gtggagaaca cttaatatgt gcatggatag ctgaaggttt tgtacatggg caagaggtag    8220
```

```
cagagaccta ccttagtgat ctagtaaaaa agaaattaat cgatgcagtg gaggttgatg   8280
ctggaggaaa ggtcctcacg tgccgcatgt atgacttggt gcatgacttt atcgtctcaa   8340
aatcaattga agaacgattt gtttatattt taaatgactc ggaaggcaga gatttgtcag   8400
aagcagttca cgttcaccag cgactataca tccaggaca taataacaaa gaactagacc    8460
tgcaaattcc ttggctgccc caagtgaagt cacttgtctc ctgtggtact gcgccatcca   8520
tcttaaagtt taagggtcta catgttatgg atttagggc ctgtgaatct ttgcaggcta    8580
gtcatctcaa gggtataaat aatgtaagtt ctttgagata tctggtcata ggaggtaagt   8640
gtatctctgg catccctaag gaaattgcga agctggaaca tttgcggaca ctagatttaa   8700
gtgcaagtgg tctaaatgaa ttgccagaat atgttttcat gataagaaaa ttggaacgcc   8760
taattgttaa tagtcagatg aagatatcat atggtattgc aaagatgtct gctttacagg   8820
agctaggcga tatcaatgtc accgacccag agttgctgaa aagtctctgt aagctaacca   8880
aattgagggt tcttagaatt tccatatggt catgggatga tagtttgaag aactatttta   8940
aacaactgtg tgacaacttg cgttcactgg ttcagtgcac ggagaacatc cagagtctct   9000
ccataatgac atgctgctcc ctggttttca tggatgattt gggtgagaat tggacccctc   9060
aatgtctcca gaagctcgag gtcggttgca gcgcatttga catattgcca agttggtttg   9120
gctcactttc tagtatctcc acgttaacaa tcgaggtcta caagctgtca caggacataa   9180
ttgatacgct cggaaggctg gctggtcttg gttctctatc cctgacatcg aaacaagtac   9240
caaaaggata ctttgtgatc ggctctgaca ggttcaataa gctacagagc ttaaagtttg   9300
tgagcaatgc aatggtagag atgttttcac gtcaacaatc aaatggcacg gaacagctca   9360
aaaggcttat gattgtgttc catgcttcac gtacacaaga tgtgaacaaa gatttctgct   9420
ttggtttgga gaacctgtct tccctagagc atgttcgtgt tgaaataatt tgtttcgatg   9480
ccagccataa catggtgaaa aacgcagaag ctgcagttca gaaagctata tctggcacaa   9540
gtatcgcaaa tctggaaata cgaagacttc aggaaaatag tatgacacag gacgaagcgg   9600
acctctgtga tgcagtacaa gagcagaata atcagaagca ccagaaaatg aagaggtact   9660
aattttccac tcctacaata caacgatgtc aaataaaatt atttctcttg tattttctta   9720
taaagttcgg cccttgagag catctccaag agaggtctta aactaggtcc tatcttcaaa   9780
tataggacat aagagtaaaa catggctttg agatggatcg atagaatctc agcagcaaca   9840
ggtaaagagt tatagtaggc cttcgttaaa tgtcgccatg gatgtgattc gcaagattct   9900
ggaggttcaa tgtctgctag agctgcttca tgcccacaac cccaatttcg aacgaactca   9960
atcttaggca caacgatcc ctctgggatg tccgatttta ggtagtattc tttcgaattt   10020
aacgatatgc tgcagaaagg cattttagat cccacgtagc taggcgccca ggcatagccg   10080
aacagaccca aactcgcgtt cggacgctca gttatgcagt catgctaggt ctcatcactg   10140
atgatgtaat gcagaattta tgcaacgggg gactggcaac tggaaatagc acataggtct   10200
gtagaatcag atgagtagct gaaaggttaa tattctgaat ttcagagtta ttactaatat   10260
atggctattg gtgtactatt ctacctactg tcactaattg aaatgtctct tgttatacct   10320
atgtgtgatg atgtatttgt gaaacattcc atatgcccga cataaaatca ttgatattgt   10380
ttatgggatt attgttaaga tggatgtatg attattggca ttgagttgtt tcaactagcc   10440
cttcatcgct agctacattt tcatggatg cttgtttgaa tagtacttgc aatatgcttc   10500
aactagatgg aatgctcgga tactgatatg ctactatgta ttcctatttt gcagttctat   10560
```

```
ggagtcccag gatgggtacc tcacttcttt accgaaccag gaaagtgcag atgttgttgg    10620
ctccgatagt attgtggaac cactagtgaa tgaaatgaac tcgcagacaa ttaagaggga    10680
tcaatccacg aatttcagtg aagatgagga cttaatgttg gtttctagct accttaatgt    10740
aagcaaagat tctattactg gaagggataa aaagaaggc acattttggg aaagagtatg     10800
ggaatactat aacaagaata ggacattcga gtccgatcat agttggtcgt cattgaaaca    10860
tcgctggctt gcaattcaga aggaagtgaa tatctttcaa ggttactatg atgccataga    10920
aaggaaaaat caaagtggcc agacaagtga tgacaaggtg aatcatacat tttgtaccat    10980
tatttatact tcttaacata acatgcaact tctcacattt gtgaatcctg tgttgttttg    11040
tagcatgctg aagcagaagt agaattccga gaaaaacaag ggaaggcttt ttctgtattc    11100
catgtgtgga tgattctaag gcatgagcca aagtgggcat ttagagaatc aaagatcaaa    11160
gaccagcatg aagcaaacaa tgctaatact gatgctcctg ccaacattta tagaccacag    11220
gggaggaaag ctgagaagga aaaggctcgt gcgagaaagc atggtggatc tgatgttgat    11280
ggtgatccgt tcatcgaaga agtaaaaaat atgagggaag cacggaaga aacagaacga     11340
gaccgaaaga cccatgatga caagttctat gagttggaaa agagtaagct tgaattggag    11400
cgagatcgac atgacaaaga gataatgcaa acagacacaa gcacaatgga tgaagaatcg    11460
aaacaatact tcaagttgat gaaacaagag attttggctc gccgtttcgg gagtagtcag    11520
ccatagttgt tagctgttgg aaacttagat agtattttgt ttttgccaga catctgttat    11580
tgataatctt gtgaactttt acatatggca cctgtcaact acttcctcct ttctaaaata    11640
ttattcgttt tagggtgtta atagattcat acaatatttg atgtatgtat tttatatatg    11700
tgtctagatt cgttgtctaa gggtcttcta gtctggcatt gcctgtacag tcataatttg    11760
agcacttcct attttgtttg gtggaaagta ctgtgatcac tttcattgcc tctgctttat    11820
tgtaccatgc taaactgggt cgattactta agtctttata aaacaactat catgaagcat    11880
catataaaca aaactgagct gatttatttta agtcttgttc attgctgtag actgtaactg    11940
aatcgattct gggtatttca agaaaactgc aacttgaacg atcagaatta ctggaaaatt    12000
cttccggcaa aagaggacaa acgaattgct agaaaattta atgccttttt ctcgaatcaa    12060
cgtaacacct ttgtcccttc acgggctcct taatgcatct ggtacttctt tttagtactg    12120
ttctatactc cctctgttac aattttttt ttgattttt acctcaagtt tgaccagttc      12180
gacctattaa aaaacttcat aattatcgtt aattttacg gtgatatctt tagcacataa     12240
tatactttaa gctaaagtat gactttgatt tttcatcttt ttgcaatttt ttgaataata   12300
agagctggtc aaatttaaca aaaaaaatca aacgaattat aaattaaaac gaagatagta    12360
atatatatat ataggaga aggtaatgga agcccagagc ttccattaat accgggaagt      12420
cccggccagg cagaccccac acacattttg cgggctaggt cgacgtgcgc ccgatgcgcc    12480
tgtttctggt tcgagcagat cagagcataa aatataaact aaaacaacat aaacgactac    12540
aagttttagc gtaaattggg aatctgtttc gtaacagagc gtggcggcgt gaaaatcggc    12600
catgcagagc ccgcacgcgt gttttccggg ctgggccggc gtgggcccga tgcgcctatt    12660
tc                                                                   12662
```

<210> SEQ ID NO 5
<211> LENGTH: 7811
<212> TYPE: DNA
<213> ORGANISM: Zea mays
<400> SEQUENCE: 5

```
atggagttcg caactggagc gctaggcacc cttcttctca agctctccat gctgcttcat    60
ggtgagtaca acctggagaa gggcgtcagg ggggacatcc agcgcgtcat gaacaagctc   120
gagcgggttc attctgtcct cggccatgtt gtcgaagtgc ctgtgccact gaagccacgt   180
cctgatctgg tcagaatgtt ggcacgcagc gtcaggagc tatcctacga catggaggac   240
ttcgtcgaca ccttcctggt gcgtgtccaa ggccctgaac gcaccagcaa agaagcgcc   300 aaaatattca tgaataagac atatatggtc gtgaatcgcc atgagatcgc ccagaccatc   360
aaggacttcg aagagcgcgt ccagcagata gatgagcgtc gtcaaaggtc attgaaacac   420
ttaatttcca ctttggcttg cgtgcatatg aactttcacc tttactgtct ttcttccatt   480
ttatttcctt ttctggttct aacaggtacg atgttgatgc tatggttccc cgtgtcaaaa   540
ccttggttga tcctcgcata tttgctctga agtacaccaa ggccacggac cttgtcggca   600
tggatgaggc aagggaggaa ctaatcacaa ggttgaccaa ggaagatgac acctccactg   660
aacaaaggcg agtctctatc gttggttttg gaggacttgg caagacagcg cttgcaaaag   720
cagtttatga caaacttaaa gctaaagggg aattccattg cgcggccttt gtgtcggtgt   780 ctcggttttcc tcagctcgaa aaattcttca aggaattgct ttatgagctt gacgagactg   840
agtacaagga acttattgac atcagcaccc cattggaact tatgaatcta gtgcatgaat   900
tccttcataa taagaggtac acgcgtacat gtaccacacc tagtgtgcat tatatgttca   960
ttccacggaa atatccatat tatagagtaa tatgcttata tatattattg caattcatat  1020
ctttagctat gcttacatta cttctccaat taatacaata aatataggta ccttattgct  1080
gtcgatgaca tatgggatac tgacgcatgg gcaatgatac aatgggcttt tcctgagaat  1140
aagctaggaa gcagaataat cgcaactact cgcagaattg atgttgctga gtatgtaggt  1200
ggttgctata tgatgaaacc tcttactcga gagaaatcaa atatattatt ctatggacga  1260
atatttggct ctgaaggtaa atgtcctcct gaactttctg atgcgtctga gaaaatattg  1320
aataaatgcg gaggcgtgcc attggctatt attactacat ctagcttgct ggctagtaag  1380
tcaagaaaca taaagaatg gtacaatgtt gctgattcta ttggttccag aatactaaaa  1440
aacagtactg aaatggagaa tatgaggaac atactgctgc ttagctatta tgatctacca  1500
gcacgattaa agacatgttt gttatatctg agtattttcc ctgaagattg tgagattggg  1560
atgcatcggt taatatggag gtggatagct gaaggttttt tcaatggaga actagcacat  1620
gatgggctct ttaaccttgg cgaatcttgt ttccacgagc tcataagaag aagcatggtg  1680
cagccagtaa cacttgaagg cacgggtctt gtatatgctt gtcgtgttca taatatgttt  1740
catgatttga tcctttccgt gtcacatgaa gaagaatttg tttctgtagt caatgaaaaa  1800
tttggtcctc ttgatgttcg ttctcggcgg ttagcattcc agaacataac aaaagagcag  1860
tacagacttg tggaacatcc acggctggca caattgaggt cacttaatgc cattggatgt  1920
cctatatacg cgatacctcc aattgaaagc tataaattat tgcgtgtact ggattttcgaa  1980 aattgtgcag gtattgaagg ccatgatctt gttcatcttg ggaaattgca tcacctcaag  2040
ttccttgggc taagaaacac gtttatcggt aagctgccgg aaggaatagg gaaccctcaag  2100 tttctgcaaa cattggaccct cgatggaact ggtgtggaag aattacctca agccttgcat  2160
aatcttacag aattgatgtg cctaattgct gactggagaa cgagagtgcc caattggatt  2220 ggtaaccctca cgtccctgca gcacttggtg atttatcctg gtgggcatga cgatgaggat  2280
tctgcgagca ggtttgttaa tgagctggga aagctgagac aactaagggt gctccgtttt  2340
```

```
ttgataaaag cacaagatga acggcagctg agagatttgc tagagtccct atcgaatctg    2400
ccagagatcg aggctataca ttttgattac tatggagtac agttaaatag aggtgttcag    2460
ttggaacctg aaggctatgc cctctctaga gatattcgtt ccttggaatt gcgctggttg    2520
gagttctcaa ggctgcctct ttggattaat cctggacatc ttcctaacct ctactactta    2580
tggctgatgg tatctgaggc ggaagagcgg gatctggaaa tccttggggg gtttccagtg    2640
cttcactccc tccacttgtt gattgtgaat actgaacgtg aagatgtcat gacttgtggc    2700
tgtggtggat tcaagaattt gaaatgctgc agtataacta aaccgctgaa atttgtacat    2760
ggagctatgc ccaggcttga agtcctcgat ttccatttca gtgtgcaact cctaacggat    2820
tcaaaccaag atttttgattt tgactttggc ttgggaaacc tacattggct tcagcaagcc    2880
atcgttcaaa tcacagccct ggtgaggag gtggagtctg ggggagagc acaggtggct    2940 ctgcgggatg caatacgtac ccatcccaac cgtcctaccc ttgaaataaa cttatttggg    3000
caaacaatac ctccagagtt accaaaggtc aggactcttt gtcatctctc tctcacctca    3060
tttcgttgtc ttgttttcgt ttgccttatt tcactgtttc agcaagacga cgatggagcg    3120
aaaattgtgg agatatcacc ggccgagagt agtcgtcaag ctcaagagcg ggagaaaaga    3180
aacatcgatg tggcgatgaa gaatgcaaca cgggtgccgt cttttttacac aaagtcatca    3240 attgatgagc caatggatca gctcataaac atgctatctg tggttgatga cgaagcctac    3300
actaagaaca taaagatact atctattgta aggtctgagg gactggggaa gactactctg    3360
gcccaaaaag cattcgaaga gctccattcg caatttgacc gtggggcgtt cgttctacta    3420
ggccagaatc ctgacttgag gagagtcttt gctgacattc tccgtggtct tgacaagcaa    3480
aggtacatag attttccagt ggcaatattg gatctagtgg acctgatctg gctagtccgt    3540
aaatcgctca taaacaaaag gtatgtccaa cccactaaca tgctagtact acctttattc    3600
agctatatat ttgctcaata tattgtctcc gttcttttt ttatttgacg tggttgatta    3660 tttttttcttc aaaattctaa tcactcgtgt gctaaaaaaa atctgggtgt tatatccatg    3720
agtgttattt tgacactgcc ggttaaaccg gtgagtattg atttctctga ttttgctttg    3780
tttgacttgg ttcttcttgg tgtcttcacc atttcatccc atagacctat aaacctgaga    3840
atatacatct agaaaacatt gttaatctaa gtgttgtgtg tcaatcaatc accaaaacga    3900
agcaccgaaa tatgacataa agaccatttt tgctacagtt gttgtcagta gtagttacta    3960
ctaaatatgg attataaccc ttggatatta ttattttttcc aggttctttta ttgtatttga    4020 tgatatatgt gatgtaaaag catgggaaat tataaaatgc gctttgattg aaaataacaa    4080
ccacagtgta gttcttacga caagtcgcaa cactggtatt actgaaatta ttggtggcag    4140
caagcaatta caacctctat cagcaactat ctctaaaaat ctactctgca aaaggttatt    4200
tggatcggca ggcaagtgtc cttctgaact agtaaatata tgtgacaatc ttgtagaaga    4260
atgtggtgga atactatctg tgatcgacga aactgtgaca ttgcttgcaa gtataccacc    4320
aacagtggag aactgggagg cagtgtacgc cagaagaatg ttggatcggt cttatcctgg    4380
tttaactgac agtctaaaga attgcttact ctattttact atgtttcgaa gaggacatga    4440
gattagtgga gaacacttaa tatgtgcatg gatagctgaa ggttttgtac atgggcaaga    4500
ggtagcagag acctacctta gtgatctagt aaaaaggaaa ttaatcgatg cagtggaggt    4560
tgatgctgga ggaaaggtcc tcacgtgccg catgtacgac ttggtgcatg actttatcgt    4620 ctcaaaaatca attgaagaac gatttgttta tattttaaat gactcggaag gcagagattt    4680
gtcagaagca gttcatgttc accagcgcct atacatccag ggacataata acaaagaact    4740
```

```
agatctgcaa attccttggc tgccccaagt gaagtcactt gtctcctgtg gtactgcgcc    4800
atccatctta aagtttaagg gtctacatgt tatggattta ggggcctgtg aatctttgca    4860
ggctagtcat ctcaagggta taaataatgt aagttctttg agatatctgg tcataggagg    4920
taagtgtatc tctggcatcc ctaaggaaat tgcgaagctg aacatttgc ggtcactaga     4980 tttaagtgca agtggtctaa atgaattgcc agaatatgtt ttcatgataa gaaaattgga    5040
acgcctaatt gttaatagtc agatgaagat atcatatggt attgcaaaga tgtctgcttt    5100
acaggagcta ggcgatatca atgtcactga cccagagttg ctgaaaagtc tctgtaagct    5160
aatcaaattg agggttctta gaatttccat atggtcatgg gatgatagtt tgaagaacta    5220
ttttaaacaa ctgtgtgaca acttgcgttc actggttcag tgcacggaga acatccagag    5280
tctctccata atgacatgct gctccctggt tttcatggat gatttgggtg agaattggac    5340
ccctcaatgt ctccagaagc tcgaggtcgg ttgcagcgca tttgacatat gccaagttg     5400 gtttggctca ctttctagta tctccacgtt aacaatcgag gtctacaagt tgtcacagga    5460
cataattgat acgctcggaa ggctgcctgg tcttggatct ctatccctga catcgaaaca    5520
agtaccaaaa ggatactttg tgatcggctc tgacaggttc aataagctac agagcttaaa    5580
gtttgtgagc aatgcgatgg tagagatgtt tccacgtcaa caatcaaatg gcacggaaca    5640
gctcaaaagg cttatgattg tgttccatgc ttcacgtaca caagatgtga acaaagattt    5700
ctgctttggt ttggagaacc tgtcttccct agagcatgtt cgtgttgaaa taatttgttt    5760
cgatgccagc cataacatgg tgaaaaacgc agaagctgca gttcggaaag ctatatctgg    5820
cacaagtatc gcaaatctgg aaatacgaag acttcaggaa aatagtatga cacaggacga    5880
agcggacctc tgtgatgcag tacaagagca gaataatcag aagcaccaga aaatgaagag    5940 gtactaatt tccactccta caatacaacg atgtcaaata aaattatttc tcttgtattt     6000
tcttataaag ttcggccctt gagagcatct ccaagagagg tcttaaacta ggtcctatct    6060
tcaaatatag gacataagag taaaacatgg ctttgagatg gatcgataga atctcagcag    6120
caacaggtaa agagttatag taggccttcg ttaaatgtcg ccatggatgt gattcgcaag    6180
attctggagg ttcaatgtct gctagagctg cttcatgccc acaaccccaa tttcgaacga    6240
actcaatctt aggcaacaac gatccctctg ggatgtccga ttttaggtag tattctttcg    6300
aatttaacga tatgctgcag aaaggcattt tagatcccac gtagctaggc gcccaggcat    6360
agccgaacag acccaaactc gcgttcggac gctcagtcat gcagtcatgc taggtctcat    6420
cactgatgat gtaatgcaaa atttatgcaa cgggggactg gcaactggaa atagcacata    6480
ggtctgtaga atcagatgag tagctgaaag gttaatattc tgaatttcag agttattact    6540
aatatatggc tattggtgta ctattctacc tactgtcact aattgaaatg tctcttgtta    6600
tacctatgtg tgatgatgta tttgtgaaac attccatatg cccgacataa aatcattgat    6660
attgtttatg ggattattgt taagatggat gtatgattat tggcattgag ttgtttcaac    6720
tagcccttca tcgctagcta catttctcat ggatgcttgt ttgaatagta cttgcaatat    6780
gcttcaacta gatggaatgc tcggatactg atatgctact atgtattcct attttgcagt    6840
tctatggagt cccaggatgg gtacctcact tctttaccga accaggaaag tgcagatgtt    6900
gttggctccg ataatattgt ggaaccacta gtgaatgaaa tgaactcgca gacaattaag    6960
agggatcaat ccacgaattt cagtgaagat gaggacttaa tgttggtttc tagctacctt    7020
aatgtaagca aagattctat tactggaagg gataaaaaag aaggcacatt ttgggaagaa    7080
```

```
gtatgggaat actataacaa gaataggaca ttcgagtccg atcatagttg gtcgtcattg    7140
aaacatcgct ggcttgcaat tcagaaggaa gtgaatatct ttcaaggtta ctatgatgcc    7200
atagaaagga aaaatcaaag tggccagaca agtgatgaca aggtgaatca tacattttgt    7260
accattattt atacttctta acataacatg caacttctca catttgtgaa tcctgtgttg    7320
ttttgtagca tgctgaagca gaagtagaat tccgagaaaa acaagggaag gcttttctg     7380 tattccatgt gtggatgatt ctaaggcatg agccaaagtg ggcatttaga gaatcaaaga    7440
tcaaagacca gcatgaagca aacaatgcta atactgatgc tcctgccaac atttatagac    7500
cacaggggag gaaagctgag aaggaaaagg ctcgtgtgag aaagcatggt ggatctgatg    7560
ttgatggtga tccgttcatt gaagaagtaa aaaatatgag ggaagcacgg gaagaaacag    7620
aacgagaccg aaagacccat gatgacaagt tctatgagtt ggaaaagagt aagcttgaat    7680
tggagcgaga tcgacatgac aaagagataa tgcaaacaga cacaagcaca atggatgaag    7740
aatcgaaaca atacttcaag ttgatgaaac aagagatttt ggctcgccgt ttcgggagta    7800
gtcagccata g                                                         7811

<210> SEQ ID NO 6
<211> LENGTH: 101
<212> TYPE: DNA
<213> ORGANISM: Zea mays
<220> FEATURE:
<221> NAME/KEY: misc_feature
<222> LOCATION: (51)..(51)
<223> OTHER INFORMATION: n is c or t

<400> SEQUENCE: 6
ttgatctcgc ccttattctc cgggaggctg ccggggtcct ccgactgcag naggtggacg    60
ccgatcccgt agttgaacag cctgctagat tgtgttgtat a                        101

<210> SEQ ID NO 7
<211> LENGTH: 101
<212> TYPE: DNA
<213> ORGANISM: Zea mays
<220> FEATURE:
<221> NAME/KEY: misc_feature
<222> LOCATION: (51)..(51)
<223> OTHER INFORMATION: n is a or c

<400> SEQUENCE: 7
attgttgttt ccattatgct actctgggtc ttatggacaa ggccccggcc nggaaaaaga    60
agaaggggcg aaagagctca gtcaagctgt ccaaaaatgt t                        101

<210> SEQ ID NO 8
<211> LENGTH: 85
<212> TYPE: DNA
<213> ORGANISM: Zea mays
<220> FEATURE:
<221> NAME/KEY: misc_feature
<222> LOCATION: (35)..(35)
<223> OTHER INFORMATION: n is g or t

<400> SEQUENCE: 8
tatgattcac cttgtcatca cttgtctggc cactntgatt tttcctttct atggcatcat    60
agtaaccttg aaagatattc acttc                                          85

<210> SEQ ID NO 9
<211> LENGTH: 53
<212> TYPE: DNA
<213> ORGANISM: Zea mays
```

```
<220> FEATURE:
<221> NAME/KEY: misc_feature
<222> LOCATION: (30)..(30)
<223> OTHER INFORMATION: n is a or c

<400> SEQUENCE: 9
gcacayaygc aacaaccgta cactgcaagn ctcccttcca atgcattayr aat              53
```

METHODS OF IDENTIFYING, SELECTING, AND PRODUCING ANTHRACNOSE STALK ROT RESISTANT CROPS

CROSS-REFERENCE TO RELATED APPLICATIONS

This application is a 35 U.S.C. § 371 national stage application of PCT International Application No. PCT/US2020/046665, filed Aug. 17, 2020, which claims the benefit of U.S. Provisional Application No. 62/890,729, filed Aug. 23, 2019, each of which is incorporated by reference herein in its entirety.

FIELD

The field is related to plant breeding and methods of identifying and selecting plants with resistance to anthracnose stalk rot. Provided are methods to identify novel genes that encode proteins providing plant resistance to anthracnose stalk rot and uses thereof. These disease resistant genes are useful in the production of resistant plants through breeding, transgenic modification, or genome editing.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 8054_Seq_List.txt, a creation date of Aug. 22, 2019, and a size of 63 Kb. The sequence listing filed via EFS-Web is part of the specification and is hereby incorporated in its entirety by reference herein.

BACKGROUND

Anthracnose stalk rot caused by the fungal pathogen *Colletotrichum graminicola* (Ces.) Wils, (Cg) is one of the major stalk rot diseases in maize (*Zea mays* L.). Anthracnose stalk rot is a major concern due to significant reduction in yield, grain weight and quality. Yield losses occur from premature plant death that interrupts filling of the grain and from stalk breakage and lodging that causes ears to be lost in the field. Anthracnose stalk rot occurs in all corn growing areas and can result in 10 to 20% losses.

Farmers can combat infection by fungi such as anthracnose through the use of fungicides, but these have environmental side effects and require monitoring of fields and diagnostic techniques to determine which fungus is causing the infection so that the correct fungicide can be used. The use of corn lines that carry genetic or transgenic sources of resistance is more practical if the genes responsible for resistance can be incorporated into elite, high yielding germplasm without reducing yield. Genetic sources of resistance to Cg have been described (White, et al. (1979) Annu. Corn Sorghum Res. Conf. Proc. 34:1-15; Carson. 1981. Sources of inheritance of resistance to anthracnose stalk rot of corn. Ph.D. Thesis, University of Illinois, Urbana-Champaign; Badu-Apraku et al., (1987) Phytopathology 77:957-959; Toman et al. 1993. Phytopathology, 83:981-986; Cowen, N et al. (1991) Maize Genetics Conference Abstracts 33; Jung, et al., 1994. Theoretical and Applied Genetics, 89:413-418). However, introgression of resistance can be highly complex.

Selection through the use of molecular markers associated with the anthracnose stalk rot resistance trait allows selections based solely on the genetic composition of the progeny. As a result, plant breeding can occur more rapidly, thereby generating commercially acceptable maize plants with a higher level of anthracnose stalk rot. There are multiple QTL controlling resistance to anthracnose stalk rot (e.g. rcg1 and rcg1b genes on chromosome 4 (WO2008157432 and WO2006107931)), with each having a different effect on the trait. Thus, it is desirable to provide compositions and methods for identifying and selecting maize plants with newly conferred or enhanced anthracnose stalk rot resistance. There is a continuous need for disease-resistant plants and methods to find disease resistant genes.

SUMMARY

Compositions and methods useful in identifying and selecting plant disease resistance genes, or "R genes," are provided herein. The compositions and methods are useful in selecting disease resistant plants, creating transgenic resistant plants, and/or creating resistant genome edited plants. Plants having newly conferred or enhanced resistance various plant diseases as compared to control plants are also provided herein. In some embodiments, the compositions and methods are useful in selecting Anthracnose Stalk Rot (ANTROT) disease resistant plants, creating transgenic anthracnose stalk rot resistant plants, and/or creating anthracnose stalk rot resistant genome edited plants.

An anthracnose stalk rot resistant plant may be crossed to a second plant in order to obtain a progeny plant that has the resistant gene allele. The disease resistance may be newly conferred or enhanced relative to a control plant that does not have the favorable allele. The anthracnose stalk rot R gene allele may be further refined to a chromosomal interval defined by and including defined markers. In some embodiments, the methods for identifying and/or selecting plants having resistance to anthracnose stalk rot are presented. In some embodiments, the methods for identifying and/or selecting plants having resistance to anthracnose stalk rot comprise detecting or selecting a genomic region comprising SEQ ID NO: 3 (from maize line TZI8) or SEQ ID NO: 5 (from maize line MS14), the genomic region with promoter and terminator of SEQ ID NO: 4. The anthracnose stalk rot resistance may be newly conferred or enhanced relative to a control plant that does not have the favorable allele. In a further embodiment, the anthracnose stalk rot resistant region comprises a gene encoding an NLR02 polypeptide that confers or enhances resistance to anthracnose stalk rot (the "NLR02 gene"). In some embodiments, the NLR02 polypeptide comprises the amino acid sequence as set forth in SEQ ID NO: 2.

In another embodiment, methods of identifying and/or selecting plants with ANTROT resistance are provided in which one or more marker alleles linked to and associated with any of: a "C" at Left Flanking (Conservative)_Marker 104 (position 51 of reference sequence SEQ ID NO: 6); an "A" at Right Flanking (Conservative)_Marker 015 (position 51 of reference sequence SEQ ID NO: 7); a "T" at Left Flanking (Optimistic)_Marker 115 (position 35 of reference sequence SEQ ID NO: 8); and a "C" at Right Flanking (Optimistic)_Marker 157 (position 30 of reference sequence SEQ ID NO: 9), are detected in a plant, and a plant having the one or more marker alleles is selected. The one or more marker alleles may be linked by 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, or 0.1 cM or less on a single meiosis based genetic map. The selected plant may be crossed to a second plant to obtain a progeny plant that has one or more marker alleles linked to and associated with any of a "C" at Left Flanking (Conservative)_Marker 104 (position 51 of reference sequence SEQ ID NO: 6); an "A" at Right Flanking (Conservative)_Marker 015 (position 51 of reference sequence SEQ ID NO: 7); a "T" at Left Flanking (Optimistic)_Marker 115 (position 35 of reference sequence SEQ ID NO: 8); and a "C" at Right Flanking (Optimistic)_Marker 157 (position 30 of reference sequence SEQ ID NO: 9).

In another embodiment, methods of introgressing a QTL associated with anthracnose stalk rot resistance are presented herein. In these methods, a population of plants is screened with one or more markers to determine if any of the plants has a QTL associated with anthracnose stalk rot resistance, and at least one plant that has the QTL associated with anthracnose stalk rot resistance is selected from the population. The QTL comprises a "C" at Left Flanking (Conservative)_Marker 104 (position 51 of reference sequence SEQ ID NO: 6); an "A" at Right Flanking (Conservative)_Marker 015 (position 51 of reference sequence SEQ ID NO: 7); a "T" at Left Flanking (Optimistic)_Marker 115 (position 35 of reference sequence SEQ ID NO: 8); and a "C" at Right Flanking (Optimistic)_Marker 157 (position 30 of reference sequence SEQ ID NO: 9).

In some embodiments, introgression of anthracnose stalk rot resistant genes from resistant to susceptible lines may be achieved either by marker-assisted trait introgression, transgenic, or genome editing approaches.

Embodiments include an isolated polynucleotide comprising a nucleotide sequence encoding a NLR02 polypeptide capable of conferring resistance to anthracnose stalk rot, wherein the NLR02 polypeptide has an amino acid sequence of at least 50%, at least 75%, at least 80%, at least 85%, at least 90%, at least 95% identity, at least 96% identity, at least 97% identity, at least 98% identity, or at least 99% identity when compared to SEQ ID NO: 2. In another embodiment, an isolated polynucleotide comprises a nucleotide sequence encoding a NLR02 polypeptide capable of conferring resistance to ANTROT, wherein the NLR02 polypeptide has an amino acid sequence of at least 50%, at least 75%, at least 80%, at least 85%, at least 90%, and at least 95% sequence identity, when compared to SEQ ID NO: 2. In some embodiments, the polynucleotide encoding an NLR02 polypeptide comprises a nucleic acid sequence having at least 50%, at least 75%, at least 80%, at least 85%, at least 90%, and at least 95% sequence identity to SEQ ID NO: 1.

Additional embodiments of the present disclosure include a vector comprising a polynucleotide of the disclosure, such as SEQ ID NO: 1, or a recombinant DNA construct comprising a polynucleotide disclosed herein operably linked to at least one regulatory sequence. A plant cell, as well as a plant, each comprising the recombinant DNA construct of an embodiment disclosed herein, and a seed comprising the recombinant DNA construct are also embodied.

In some embodiments, the compositions and methods relate to a modified plant having increased resistance to a disease, wherein the allele causing the increased disease resistance comprises a nucleotide sequence encoding a NLR02 resistance gene, wherein the NLR02 resistance gene is at least 50%, at least 75%, at least 80%, at least 85%, at least 90%, and at least 95% identity, at least 96% identity, at least 97% identity, at least 98% identity, or at least 99% identity to the sequence set forth in SEQ ID NO: 2.

The methods embodied by the present disclosure relate to a method for transforming a host cell, including a plant cell, comprising transforming the host cell with the polynucleotide of an embodiment of the present disclosure; a method for producing a plant comprising transforming a plant cell with the recombinant DNA construct of an embodiment of the present disclosure and regenerating a plant from the transformed plant cell, and methods of conferring or enhancing disease resistance, comprising transforming a plant with the recombinant DNA construct disclosed herein.

Methods of altering the level of expression of a protein capable of conferring disease resistance in a plant or plant cell comprising (a) transforming a plant cell with a recombinant DNA construct disclosed herein and (b) growing the transformed plant cell under conditions that are suitable for expression of the recombinant DNA construct wherein expression of the recombinant DNA construct results in production of altered levels of a protein capable of conferring disease resistance in the transformed host are also embodied.

Plants identified and/or selected using any of the methods presented above are also provided.

DESCRIPTION OF FIGURES

FIG. 1 shows PH12P9/TZI8 NLS in the PH1V69 Background. NILs negative (left) and positive (right) for the TZI8 Chr06 region.

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The NBS-LRR ("NLR") group of R-genes is the largest class of R-genes discovered to date. In *Arabidopsis thaliana*, over 150 are predicted to be present in the genome (Meyers, et al., (2003), Plant Cell, 15:809-834; Monosi, et al., (2004), Theoretical and Applied Genetics, 109:1434-1447), while in rice, approximately 500 NLR genes have been predicted (Monosi, (2004) supra). The NBS-LRR class of R genes is comprised of two subclasses. Class 1 NLR genes contain a TIR-Toll/Interleukin-1 like domain at their N' terminus; which to date have only been found in dicots (Meyers, (2003) supra; Monosi, (2004) supra). The second class of NBS-LRR contain either a coiled-coil domain or an (nt) domain at their N terminus (Bai, et al. (2002) Genome Research, 12:1871-1884; Monosi, (2004) supra; Pan, et al., (2000), Journal of Molecular Evolution, 50:203-213). Class 2 NBS-LRR have been found in both dicot and monocot species. (Bai, (2002) supra; Meyers, (2003) supra; Monosi, (2004) supra; Pan, (2000) supra).

The NBS domain of the gene appears to have a role in signaling in plant defense mechanisms (van der Biezen, et al., (1998), Current Biology: CB, 8:R226-R227). The LRR region appears to be the region that interacts with the pathogen AVR products (Michelmore, et al., (1998), Genome Res., 8:1113-1130; Meyers, (2003) supra). This LRR region in comparison with the NB-ARC (NBS) domain is under a much greater selection pressure to diversify (Michelmore, (1998) supra; Meyers, (2003) supra; Palomino, et al., (2002), Genome Research, 12:1305-1315). LRR domains are found in other contexts as well; these 20-29- residue motifs are present in tandem arrays in a number of proteins with diverse functions, such as hormone-receptor interactions, enzyme inhibition, cell adhesion and cellular trafficking. A number of recent studies revealed the involvement of LRR proteins in early mammalian development, neural development, cell polarization, regulation of gene expression and apoptosis signaling.

An allele is "associated with" a trait when it is part of or linked to a DNA sequence or allele that affects the expression of the trait. The presence of the allele is an indicator of how the trait will be expressed.

As used to herein, "disease resistant" or "have resistance to a disease" refers to a plant showing increase resistance to a disease compared to a control plant. Disease resistance may manifest in fewer and/or smaller lesions, increased plant health, increased yield, increased root mass, increased plant vigor, less or no discoloration, increased growth, reduced necrotic area, or reduced wilting. In some embodiments, an allele may show resistance one or more diseases.

Disease affecting maize plants include, but are not limited to, bacterial leaf blight and stalk rot; bacterial leaf spot; bacterial stripe; chocolate spot; goss's bacterial wilt and blight; holcus spot; purple leaf sheath; seed rot-seedling blight; bacterial wilt; corn stunt; anthracnose leaf blight; anthracnose stalk rot; aspergillus ear and kernel rot; banded leaf and sheath spot; black bundle disease; black kernel rot; borde blanco; brown spot; black spot; stalk rot; cephalosporium kernel rot; charcoal rot; corticium ear rot; curvularia leaf spot; didymella leaf spot; diplodia ear rot and stalk rot; diplodia ear rot; seed rot; corn seedling blight; diplodia leaf spot or leaf streak; downy mildews; brown stripe downy mildew; crazy top downy mildew; green ear downy mildew; *graminicola* downy mildew; java downy mildew; philippine downy mildew; sorghum downy mildew; spontaneum downy mildew; sugarcane downy mildew; dry ear rot; ergot; horse's tooth; corn eyespot; fusarium ear and stalk rot; fusarium blight; seedling root rot; gibberella ear and stalk rot; gray ear rot; gray leaf spot; cercospora leaf spot; helminthosporium root rot; hormodendrum ear rot; cladosporium rot; hyalothyridium leaf spot; late wilt; northern leaf blight; white blast; crown stalk rot; corn stripe; northern leaf spot; helminthosporium ear rot; penicillium ear rot; corn blue eye; blue mold; phaeocytostroma stalk rot and root rot; phaeosphaeria leaf spot; physalospora ear rot; botryosphaeria ear rot; pyrenochaeta stalk rot and root rot; pythium root rot; pythium stalk rot; red kernel disease; rhizoctonia ear rot; sclerotial rot; rhizoctonia root rot and stalk rot; rostratum leaf spot; common corn rust; southern corn rust; tropical corn rust; sclerotium ear rot; southern blight; selenophoma leaf spot; sheath rot; shuck rot; silage mold; common smut; false smut; head smut; southern corn leaf blight and stalk rot; southern leaf spot; tar spot; trichoderma ear rot and root rot; white ear rot, root and stalk rot; yellow leaf blight; zonate leaf spot; american wheat striate (wheat striate mosaic); barley stripe mosaic; barley yellow dwarf; brome mosaic; cereal chlorotic mottle; lethal necrosis (maize lethal necrosis disease); cucumber mosaic; johnsongrass mosaic; maize bushy stunt; maize chlorotic dwarf; maize chlorotic mottle; maize dwarf mosaic; maize leaf fleck; maize pellucid ringspot; maize rayado fino; maize red leaf and red stripe; maize red stripe; maize ring mottle; maize rough dwarf; maize sterile stunt; maize streak; maize stripe; maize tassel abortion; maize vein enation; maize wallaby ear; maize white leaf; maize white line mosaic; millet red leaf; and northern cereal mosaic.

Disease affecting plants include, but are not limited to, bacterial blight; bacterial leaf streak; foot rot; grain rot; sheath brown rot; blast; brown spot; crown sheath rot; downy mildew; eyespot; false smut; kernel smut; leaf smut; leaf scald; narrow brown leaf spot; root rot; seedling blight; sheath blight; sheath rot; sheath spot; alternaria leaf spot; and stem rot.

Disease affecting soybean plants include, but are not limited to, alternaria leaf spot; anthracnose; black leaf blight; black root rot; brown spot; brown stem rot; charcoal rot; choanephora leaf blight; downy mildew; drechslera blight; frogeye leaf spot; leptosphaerulina leaf spot; mycoleptodiscus root rot; neocosmospora stem rot; phomopsis seed decay; phytophthora root and stem rot; phyllosticta leaf spot; phymatotrichum root rot; pod and stem blight; powdery mildew; purple seed stain; pyrenochaeta leaf spot; pythium rot; red crown rot; dactuliophora leaf spot; rhizoctonia aerial blight; rhizoctonia root and stem rot; rust; scab; sclerotinia stem rot; sclerotium blight; stem canker; stemphylium leaf blight; sudden death syndrome; target spot; yeast spot; lance nematode; lesion nematode; pin nematode; reniform nematode; ring nematode; root-knot nematode; sheath nematode; cyst nematode; spiral nematode; sting nematode; stubby root nematode; stunt nematode; alfalfa mosaic; bean pod mottle; bean yellow mosaic; brazilian bud blight; chlorotic mottle; yellow mosaic; peanut mottle; peanut stripe; peanut stunt; chlorotic mottle; crinkle leaf; dwarf; severe stunt; and tobacco ringspot or bud blight.

Disease affecting canola plants include, but are not limited to, bacterial black rot; bacterial leaf spot; bacterial pod rot; bacterial soft rot; scab; crown gall; alternaria black spot; anthracnose; black leg; black mold rot; black root; brown girdling root rot; cercospora leaf spot; clubroot; downy mildew; fusarium wilt; gray mold; head rot; leaf spot; light leaf spot; pod rot; powdery mildew; ring spot; root rot; sclerotinia stem rot; seed rot, damping-off; root gall smut; southern blight; verticillium wilt; white blight; white leaf spot; staghead; yellows; crinkle virus; mosaic virus; yellows virus;

Disease affecting sunflower plants include, but are not limited to, apical chlorosis; bacterial leaf spot; bacterial wilt; crown gall; erwinia stalk rot and head rot; lternaria leaf blight, stem spot and head rot; botrytis head rot; charcoal rot; downy mildew; fusarium stalk rot; fusarium wilt; myrothecium leaf and stem spot; phialophora yellows; phoma black stem; phomopsis brown stem canker; phymatotrichum root rot; phytophthora stem rot; powdery mildew; pythium seedling blight and root rot; rhizoctonia seedling blight; rhizopus head rot; sunflower rust; sclerotium basal stalk and root rot; septoria leaf spot; verticillium wilt; white rust; yellow rust; dagger; pin; lesion; reniform; root knot; and chlorotic mottle;

Disease affecting sorghum plants include, but are not limited to, bacterial leaf spot; bacterial leaf streak; bacterial leaf stripe; acremonium wilt; anthracnose; charcoal rot; crazy top downy mildew; damping-off and seed rot; ergot; fusarium head blight, root and stalk rot; grain storage mold; gray leaf spot; latter leaf spot; leaf blight; milo disease; oval leaf spot; pokkah boeng; pythium root rot; rough leaf spot; rust; seedling blight and seed rot; smut, covered kernel; smut, head; smut, loose kernel; sooty stripe; downy mildew; tar spot; target leaf spot; and zonate leaf spot and sheath blight.

A plant having disease resistance may have 5, 10, 15, 20, 25, 30, 35, 40, 45, 50, 55, 60, 65, 70, 75, 80, 85, 90, 95, or 100% increased resistance to a disease compared to a control plant. In some embodiments, a plant may have 5, 10, 15, 20, 25, 30, 35, 40, 45, 50, 55, 60, 65, 70, 75, 80, 85, 90, 95, or 100% increased plant health in the presence of a disease compared to a control plant.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful with respect to the subject matter of the current disclosure when they demonstrate a significant probability of co-segregation (linkage) with a desired trait (e.g., resistance to ANTROT). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

An "elite line" is any line that has resulted from breeding and selection for superior agronomic performance.

An "exotic strain," a "tropical line," or an "exotic germplasm" is a strain derived from a plant not belonging to an available elite line or strain of germplasm. In the context of a cross between two plants or strains of germplasm, an exotic germplasm is not closely related by descent to the elite germplasm with which it is crossed. Most commonly, the exotic germplasm is not derived from any known elite line, but rather is selected to introduce novel genetic elements (typically novel alleles) into a breeding program.

A "favorable allele" is the allele at a particular locus (a marker, a QTL, a gene etc.) that confers, or contributes to, an agronomically desirable phenotype, e.g., disease resistance, and that allows the identification of plants with that agronomically desirable phenotype. A favorable allele of a marker is a marker allele that segregates with the favorable phenotype.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism, cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment.

The term "heterogeneity" is used to indicate that individuals within the group differ in genotype at one or more specific loci.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G.F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theon. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) Crop Sci: 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

The term "homogeneity" indicates that members of a group have the same genotype at one or more specific loci.

The term "hybrid" refers to the progeny obtained between the crossing of at least two genetically dissimilar parents.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. Offspring comprising the desired allele may be repeatedly backcrossed to a line having a desired genetic background and selected for the desired allele, to result in the allele becoming fixed in a selected genetic background. The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meiosis). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231(1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

The term "plant" includes whole plants, plant cells, plant protoplast, plant cell or tissue culture from which plants can be regenerated, plant calli, plant clumps and plant cells that are intact in plants or parts of plants, such as seeds, flowers, cotyledons, leaves, stems, buds, roots, root tips and the like. As used herein, a "modified plant" means any plant that has a genetic change due to human intervention. A modified plant may have genetic changes introduced through plant transformation, genome editing, or conventional plant breeding A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker may consist of complementary primers flanking the locus and/or complementary probes that hybridize to polymorphic alleles at the locus. A DNA marker, or a genetic marker, may also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

The term "phenotype", "phenotypic trait", or "trait" can refer to the observable expression of a gene or series of genes. The phenotype can be observable to the naked eye, or by any other means of evaluation, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

A "production marker" or "production SNP marker" is a marker that has been developed for high-throughput purposes. Production SNP markers are developed to detect specific polymorphisms and are designed for use with a variety of chemistries and platforms.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question.

A "reference sequence" or a "consensus sequence" is a defined sequence used as a basis for sequence comparison. The reference sequence for a marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. Yield is affected by both genetic and environmental factors. "Agronomics," "agronomic traits," and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Marker loci that demonstrate statistically significant co-segregation with a disease resistance trait that confers broad resistance against a specified disease or diseases are provided herein. Detection of these loci or additional linked loci and the resistance gene may be used in marker assisted selection as part of a breeding program to produce plants that have resistance to a disease or diseases.

Genetic Mapping

It has been recognized for quite some time that specific genetic loci correlating with particular phenotypes, such as disease resistance, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods are available for detecting molecular markers or clusters of molecular markers that co-segregate with a trait of interest, such as a disease resistance trait. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) population-based association analysis (i.e. association mapping) and 2) traditional linkage analysis.

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) "Protective effect of apolipoprotein-E type-2 allele for late-onset Alzheimer-disease," *Nat Genet* 7:180-184; Hastbacka et al. (1992) "Linkage disequilibrium mapping in isolated founder populations: diastrophic dysplasia in Finland," *Nat Genet* 2:204-211; Kerem et al. (1989) "Identification of the cystic fibrosis gene: genetic analysis," *Science* 245:1073-1080) and maize (Remington et al., (2001) "Structure of linkage disequilibrium and phenotype associations in the maize genome," *Proc Natl Acad Sci USA* 98:11479-11484; Thornsberry et al. (2001) "*Dwarf*8 polymorphisms associate with variation in flowering time," *Nat Genet* 28:286-289; reviewed by Flint-Garcia et al. (2003) "Structure of linkage disequilibrium in plants,"*Annu Rev Plant Biol.* 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically enhances the detection power of association mapping (Wall and Pritchard (2003) "Haplotype blocks and linkage disequilibrium in the human genome," *Nat Rev Genet* 4:587-597).

The recombinational and mutational history of a population is a function of the mating habit as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, e.g., those that have experienced a recent genetic bottleneck, tend to show a slower rate of LD decay, resulting in more extensive haplotype conservation (Flint-Garcia et al. (2003) "Structure of linkage disequilibrium in plants,"*Annu Rev Plant Biol.* 54:357-374).

Elite breeding lines provide a valuable starting point for association analyses. Association analyses use quantitative phenotypic scores (e.g., disease tolerance rated from one to nine for each line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather is independent of map position. This analysis compares the plants' phenotypic score with the genotypes at the various loci. Subsequently, any suitable map (for example, a composite map) can optionally be used to help observe distribution of the identified QTL markers and/or QTL marker clustering using previously determined map locations of the markers.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Marker loci that demonstrate statistically significant co-segregation with a disease resistance trait, as determined by traditional linkage analysis and by whole genome association analysis, are provided herein. Detection of these loci or additional linked loci can be used in marker assisted breeding programs to produce plants having disease resistance.

Activities in marker assisted breeding programs may include but are not limited to: selecting among new breeding populations to identify which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germplasm improvement activities based on presence of favorable nucleic acid sequences.

Chromosomal Intervals

Chromosomal intervals that correlate with the disease resistance trait are provided. A variety of methods are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for a disease resistance trait.

Conversely, e.g., if two markers in close proximity show co-segregation with the desired phenotypic trait, it is sometimes unclear if each of those markers identify the same gene or two different gene or multiple genes. Regardless, knowledge of how many genes are in a particular physical/genomic interval is not necessary to make or practice that which is presented in the current disclosure.

The chromosome 6 interval may encompass any of the markers identified herein as being associated with the ANTROT resistance trait including a "C" at Left Flanking (Conservative)_Marker 104 (position 51 of reference sequence SEQ ID NO: 6); an "A" at Right Flanking (Conservative)_Marker 015 (position 51 of reference sequence SEQ ID NO: 7); a "T" at Left Flanking (Optimistic)_Marker 115 (position 35 of reference sequence SEQ ID NO: 8); and a "C" at Right Flanking (Optimistic)_Marker 157 (position 30 of reference sequence SEQ ID NO: 9). Any marker located within these intervals can find use as a marker for ANTROT resistance and can be used in the context of the methods presented herein to identify and/or select plants that have resistance to ANTROT, whether it is newly conferred or enhanced compared to a control plant. In certain embodiments, markers located upstream and downstream of NLR02 gene position are very tightly linked genetically and physically and hence may be used to select the NLR02 gene for trait introgression and products development.

Chromosomal intervals can also be defined by markers that are linked to (show linkage disequilibrium with) a disease resistant gene, and $r^2$ is a common measure of linkage disequilibrium (LD) in the context of association studies. If the $r^2$ value of LD between a chromosome 7 marker locus in an interval of interest and another chromosome 7 marker locus in close proximity is greater than ⅓ (Ardlie et al., Nature Reviews Genetics 3:299-309 (2002)), the loci are in linkage disequilibrium with one another.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with the disease resistance trait, it is important to note that the marker locus is not necessarily responsible for the expression of the disease resistance phenotype. For example, it is not a requirement that the marker polynucleotide sequence be part of a gene that is responsible for the disease resistant phenotype (for example, is part of the gene open reading frame). The association between a specific marker allele and the disease resistance trait is due to the original "coupling" linkage phase between the marker allele and the allele in the ancestral line from which the allele originated. Eventually, with repeated recombination, crossing over events between the marker and genetic locus can change this orientation. For this reason, the favorable marker allele may change depending on the linkage phase that exists within the parent having resistance to the disease that is used to create segregating populations. This does not change the fact that the marker can be used to monitor segregation of the phenotype. It only changes which marker allele is considered favorable in a given segregating population.

Methods presented herein include detecting the presence of one or more marker alleles associated with disease resistance in a plant and then identifying and/or selecting plants that have favorable alleles at those marker loci. Markers have been identified herein as being associated with the disease resistance trait and hence can be used to predict disease resistance in a plant. Any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM (based on a single meiosis based genetic map) could also be used to predict disease resistance in a plant.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. In some embodiments, the methods disclosed herein produce a marker in a disease resistance gene, wherein the gene was identified by inferring genomic location from clustering of conserved domains or a clustering analysis.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. Linkage drag may also result in reduced yield or other negative agronomic characteristics even after multiple cycles of backcrossing into the elite line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics*, 88:1-6). Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide*. Academic press. pp 75-135).

Various types of SSR markers can be generated, and SSR profiles can be obtained by gel electrophoresis of the amplification products. Scoring of marker genotype is based on the size of the amplified fragment.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as SNPs do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing, and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; and Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), INVADER®. (Third Wave Technologies) and Invader PLUS®, SNAPSHOT®. (Applied Biosystems), TAQMAN®. (Applied Biosystems) and BEADARRAYS®. (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele "T" for a specific line or variety with disease resistance, but the allele 'T' might also occur in the breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. Using automated high throughput marker detection platforms makes this process highly efficient and effective.

Many of the markers presented herein can readily be used as single nucleotide polymorphic (SNP) markers to select for the NLR02 gene. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically, with respect to the fine map information described herein, one can readily use the information provided herein to obtain additional polymorphic SNPs (and other markers) within the region amplified by the primers disclosed herein. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the species, or even across other species that have been genetically or physically aligned.

In general, MAS uses polymorphic markers that have been identified as having a significant likelihood of co-segregation with a trait such as the ANTROT disease resistance trait. Such markers are presumed to map near a gene or genes that give the plant its disease resistant phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with ANTROT disease resistance may be selected for by detecting one or more marker alleles, and in addition, progeny plants derived from those plants can also be selected. Hence, a plant containing a desired genotype in a given chromosomal region (i.e. a genotype associated with disease resistance) is obtained and then crossed to another plant. The progeny of such a cross would then be evaluated genotypically using one or more markers and the progeny plants with the same genotype in a given chromosomal region would then be selected as having disease resistance.

The SNPs could be used alone or in combination (i.e. a SNP haplotype) to select for a favorable resistant gene allele associated with ANTROT disease resistance. For example, a SNP haplotype at the "C" at Left Flanking (Conservative)_Marker 104 (position 51 of reference sequence SEQ ID NO: 6); an "A" at Right Flanking (Conservative)_Marker 015 (position 51 of reference sequence SEQ ID NO: 7); a "T" at Left Flanking (Optimistic)_Marker 115 (position 35 of reference sequence SEQ ID NO: 8); and a "C" at Right Flanking (Optimistic)_Marker 157 (position 30 of reference sequence SEQ ID NO: 9), or a combination thereof.

The skilled artisan would expect that there might be additional polymorphic sites at marker loci in and around a chromosome marker identified by the methods disclosed herein, wherein one or more polymorphic sites is in linkage disequilibrium (LD) with an allele at one or more of the polymorphic sites in the haplotype and thus could be used in a marker assisted selection program to introgress a gene allele or genomic fragment of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM (on a single meiosis based genetic map) of the disease resistance trait QTL.

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Plant Compositions

Plants identified, modified, and/or selected by any of the methods described above are also of interest.

Proteins and Variants and Fragments Thereof

NLR02 polypeptides are encompassed by the disclosure. "NLR02 polypeptide" and "NLR02 protein" as used herein interchangeably refers to a polypeptide(s) having ANTROT resistance activity, and is sufficiently identical to the NLR02 polypeptide of SEQ ID NO: 2. A variety of NLR02 polypeptides are contemplated.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In some embodiments the sequence identity is against the full-length sequence of a polypeptide. The term "about" when used herein in context with percent sequence identity means +/−1.0%.

A "recombinant protein" is used herein to refer to a protein that is no longer in its natural environment, for example in vitro or in a recombinant bacterial or plant host cell; a protein that is expressed from a polynucleotide that has been edited from its native version; or a protein that is expressed from a polynucleotide in a different genomic position relative to the native sequence.

"Substantially free of cellular material" as used herein refers to a polypeptide including preparations of protein having less than about 30%, 20%, 10% or 5% (by dry weight) of non-target protein (also referred to herein as a "contaminating protein").

"Fragments" or "biologically active portions" include polypeptide or polynucleotide fragments comprising sequences sufficiently identical to an NLR02 polypeptide or polynucleotide, respectively, and that exhibit disease resistance when expressed in a plant.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments a NLR02 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the full length or a fragment of the amino acid sequence of SEQ ID NO: 2, wherein the NLR02 polypeptide has ANTROT resistance when expressed in a plant.

Methods for such manipulations are generally known in the art. For example, amino acid sequence variants of a NLR02 polypeptide may be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess the desired activity. However, it is understood that the ability of an NLR02 polypeptide to confer disease resistance may be improved by the use of such techniques upon the compositions of this disclosure.

Nucleic Acid Molecules and Variants and Fragments Thereof

Isolated or recombinant nucleic acid molecules comprising nucleic acid sequences encoding NLR02 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell; has been edited from its native sequence; or is located in a different location than the native sequence. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding NLR02 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding NLR02 polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an NLR02 polypeptide is a non-genomic sequence.

A variety of polynucleotides that encode NLR02 polypeptides or related proteins are contemplated. Such polynucleotides are useful for production of NLR02 polypeptides in host cells when operably linked to a suitable promoter, transcription termination and/or polyadenylation sequences. Such polynucleotides are also useful as probes for isolating homologous or substantially homologous polynucleotides that encode NLR02 polypeptides or related proteins.

In some embodiments the nucleic acid molecule encoding an NLR02 polypeptide is a polynucleotide having the sequence set forth in SEQ ID NO: 2, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the NLR02 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding an NLR02 polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 2, wherein the NLR02 polypeptide has ANTROT resistance activity when expressed in a plant.

In some embodiments the nucleic acid molecule encodes an NLR02 polypeptide variant comprising one or more amino acid substitutions to the amino acid sequence of SEQ ID NO: 2.

Nucleic acid molecules that are fragments of these nucleic acid sequences encoding NLR02 polypeptides are also encompassed by the embodiments. "Fragment" as used herein refers to a portion of the nucleic acid sequence encoding an NLR02 polypeptide. A fragment of a nucleic acid sequence may encode a biologically active portion of an NLR02 polypeptide or it may be a fragment that can be used as a hybridization probe or PCR primer using methods disclosed below. Nucleic acid molecules that are fragments of a nucleic acid sequence encoding an NLR02 polypeptide comprise at least about 150, 180, 210, 240, 270, 300, 330, 360, 400, 450, or 500 contiguous nucleotides or up to the number of nucleotides present in a full-length nucleic acid sequence encoding a NLR02 polypeptide identified by the methods disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the NLR02 polypeptide and, hence, retain disease resistance. "Retains disease resistance" is used herein to refer to a polypeptide having at least about 10%, at least about 30%, at least about 50%, at least about 70%, 80%, 90%, 95% or higher of the disease resistance of the full-length NLR02 polypeptide as set forth in SEQ ID NO: 2.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments a NLR02 polynucleotide encodes a NLR02 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2. In some embodiments, a NLR02 polynucleotide comprises genomic sequence, including introns, regulatory elements, and untranslated regions.

The embodiments also encompass nucleic acid molecules encoding NLR02 polypeptide variants. "Variants" of NLR02 polypeptide encoding nucleic acid sequences include those sequences that encode the NLR02 polypeptides identified by the methods disclosed herein, but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the NLR02 polypeptides disclosed herein.

The skilled artisan will further appreciate that changes can be introduced by mutation of the nucleic acid sequences thereby leading to changes in the amino acid sequence of the encoded NLR02 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on activity, as is wherein such recursive recombination is done in vitro or in vivo.

A variety of diversity generating protocols, including nucleic acid recursive recombination protocols are available. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. such activity at a desired pH, etc. This can include identifying any activity that can be detected, for example, in an automated or automatable format, by any of the assays in the art. A variety of related (or even unrelated) properties can be evaluated, in serial or in parallel, at the discretion of the practitioner.

The nucleotide sequences of the embodiments can also be used to isolate corresponding sequences from a different source. In this manner, methods such as PCR, hybridization, and the like can be used to identify such sequences based on their sequence homology to the sequences identified by the methods disclosed herein. Sequences that are selected based on their sequence identity to the entire sequences set forth herein or to fragments thereof are encompassed by the embodiments. Such sequences include sequences that are orthologs of the sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein.

In a PCR approach, oligonucleotide primers can be designed for use in PCR reactions to amplify corresponding DNA sequences from cDNA or genomic DNA extracted from any organism of interest. Methods for designing PCR primers and PCR cloning are disclosed in Sambrook, et al., (1989) *Molecular Cloning: A Laboratory Manual* (2d ed., Cold Spring Harbor Laboratory Press, Plainview, New York), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization methods, all or part of the nucleic acid sequence can be used to screen cDNA or genomic libraries. Methods for construction of such cDNA and genomic libraries are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding polypeptides or a fragment or variant thereof. Methods for the preparation of probes for hybridization and stringency conditions are disclosed in Sambrook and Russell, (2001), supra.

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and/or a regulatory sequence and a second sequence, wherein the promoter and/or regulatory sequence initiates, mediates, and/or affects transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter or regulatory sequence may be the natural sequence or alternatively a synthetic sequence. The term "foreign" as used herein indicates that the promoter is not found in the native organism into which the promoter is introduced. As used herein, the term "heterologous" in reference to a sequence means a sequence that originates from a foreign species or, if from the same species, is substantially modified from its native form in composition and/or genomic locus by deliberate human intervention. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an NLR02 polypeptide of the embodiments. In some embodiments the DNA construct comprises a polynucleotide encoding a fusion protein comprising an NLR02 polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers include, for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the plant-preferred for a particular amino acid may be derived from known gene sequences from plants.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants include, but are not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Bio/technology* 6:923-926) and Lec1 transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

Methods to Introduce Genome Editing Technologies into Plants

In some embodiments, polynucleotide compositions can be introduced into the genome of a plant using genome editing technologies, or previously introduced polynucleotides in the genome of a plant may be edited using genome editing technologies. For example, the identified polynucleotides can be introduced into a desired location in the genome of a plant through the use of double-stranded break technologies such as TALENs, meganucleases, zinc finger nucleases, CRISPR-Cas, and the like. For example, the identified polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where an ANTROT resistance NLR02 gene allele has been identified in a genome, genome editing technologies may be used to alter or modify the polynucleotide sequence. Site specific modifications that can be introduced into the desired NLR02 gene allele polynucleotide include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional disease resistant proteins in close proximity to the NLR02 polynucleotide compositions within the genome of a plant, in order to generate molecular stacks disease resistant proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

EXAMPLES

The following examples are offered to illustrate, but not to limit, the claimed subject matter. It is understood that the examples and embodiments described herein are for illustrative purposes only, and persons skilled in the art will recognize various reagents or parameters that can be altered without departing from the spirit of the disclosure or the scope of the appended claims.

Example 1. QTL Mapping

Anthracnose Stalk Rot (ANTROT), caused by the fungal pathogen *Colletotrichum graminicola* is the most common stalk disease of maize. As part of our effort to identify native maize genes that can confer resistance to ANTROT, an F1 population was created by crossing the ANTROT-resistant line TZI8 with the (moderately) susceptible line PHI12P9. The material was backcrossed to PHI12P9 to create a BC1 mapping population. The work on this mapping population was done in conjunction with efforts described in patent application WO/2015/088970, which protects a similar locus identified from inbred line PH14J. Stalks were injected with a suspension of *C. graminicola* spores (~$5 \times 10^5$ spores/ml) ~10 days after flowering and split ~4-6 weeks later. Individual plants were genotyped with SNP markers as well as phenotyped using a visual score for ANTROT severity: ANTSUM. Severity is determined based on a visual scale of 1-10, with 1 being the most resistant and 10 being highly susceptible. Scores of 1-3 are considered very resistant, scores between 4-6 are intermediate, and scores 7-10 are classified as susceptible. Our initial mapping placed the quantitative trait loci (QTL) for ANTROT resistance between 23.38 and 125.58 cM on Chr06 with a peak correlation at 82.67 cM (MZA4127-4).

Example 2. QTL Fine Mapping and Candidate Gene Identification

To fine map the resistance gene, our mapping population was further backcrossed to the susceptible parent PH12P9 to generate a BC4 segregating population and characterized these plants using the previously-described approach. Additional SNP markers were generated for fine mapping using a combination of 56K SNPs as well as exome capture data collected for TZI8 and PH12P9.

For a population of ~3,500 segregating BC4 individual recombinants, peak correlation between genotype and phenotype was at 78.88 cM on Chr06 (p-value 1.45 E-118). Plants with the TZI8 allele at 78.88 cM had a lower ANTSUM score by ~2 scores than plants with the PH12P9 allele (Table 1). Flanking markers for our conservative and optimistic intervals are indicated below (Table 2). Mapping data was analyzed with the TIBCO® Spotfire® software package (Version 7.11.0) using the Kruskal-Wallis method for comparing numeric and categorical variables.

TABLE 1

Chr06 TZI8 ANTROT QTL Fine Mapping Interval.

| Marker Name | Genetic Position (cM) | P-Value | Average ANTSUM PH12P9 Allele | Average ANTSUM TZI8 Allele | Average ANTSUM Heterozygous |
|---|---|---|---|---|---|
| 029 | 78.46 | 3.98E−07 | 4.023 | 3.591 | 4.086 |
| *104 | 78.69 | 1.59E−115 | 5.026 | 3.283 | 3.227 |
| 108 | 78.8 | 4.55E−118 | 5.036 | 3.281 | 3.209 |
| 115 | 78.88 | 1.45E−118 | 5.036 | 3.280 | 3.203 |
| *015 | 79.13 | 4.12E−108 | 5.039 | 3.293 | 3.332 |
| 030 | 79.4 | 6.05E−100 | 5.007 | 3.342 | 3.339 |
| 144 | 79.61 | 2.07E−62 | 4.938 | 3.505 | 3.543 |
| 019 | 81.65 | 5.93E−01 | 4.018 | 3.860 | 3.876 |

The p-value presented represents the correlation of the genotype at a given genetic position with the ANTROT phenotype (ANTSUM). Genetic positions are based on the Corteva B73 genome (Version 2). Flanking markers listed in Table 2 are marked with an * (the optimistic right flanking marker was added after subsequent experiments). Peak correlation between genotype and phenotype occurred at 78.88 cM on Chr06 and is shown in bold.

TABLE 2

Flanking Marker Positions for Chr06 TZI8 ANTROT QTL.

| | Genetic Position (cM) | Physical Position (bp) | PH12P9 Allele | TZI8 Allele | SEQ ID NO: |
|---|---|---|---|---|---|
| Left Flanking (Conservative)_Marker104 | Chr06-78.69 | 133129280 | T | C | 6 |
| Right Flanking (Conservative)_Marker015 | Chr06-79.13 | 133685620 | C | A | 7 |
| Left Flanking (Optimistic)_Marker115 | Chr06-78.88 | 133369833 | G | T | 8 |
| Right Flanking (Optimistic)_Marker157 | Chr06-78.88 | 133380242, 133380887 | A | C | 9 |

Positions are based on the Corteva B73 genome (Version 2), and physical positions are also included for the public B73 genome (Version 4).

To obtain candidate genes in our mapping interval, a PacBio® whole genome sequence generated from a near isogenic line (NIL) was used in the Chr06 region with TZI8 as the donor and PH12P9 as the recurrent parent. Based on FGENESH gene model predictions, there are two Nucleotide-binding site-Leucine-Rich repeat (NLR) genes and one Wall-associated Kinase (WAK) in our indicated conservative genetic interval. These are the only genes in our interval in gene families with known roles in host defense against pathogens. RNASeq reads from TZI8 NILs were aligned to the genome to confirm our predicted gene models.

One of the two NLR genes (NLR02) is a unique fusion of two NLRs, which has unexpected evidence of expression in TZI8 but does not appear to be functional in B73. This was the only gene candidate in our optimistic mapping interval. The other NLR (NLR01) and WAK were ruled out by our indicated optimistic flanking markers.

Since the two NLRs are immediately adjacent, it was very difficult to find recombinants between these two genes. There are only four individual recombinants that suggest that NLR01 is outside our QTL interval, maintaining the possibility that this gene could be involved with resistance at the TZI8 locus. However, NLR01 is 100% identical to several susceptible lines, including B73 and PH1V69, at both the gene and protein level. Therefore, the NLR01 gene was not advanced in testing. Three recombinant families indicate that the QTL is to the left of Marker 157, ruling out the WAK. This marker occurs twice within a very small interval as indicated above (Table 1). Both positions are to the left of the WAK. However, our more conservative interval still includes this gene.

Example 3. QTL Mapping in Additional c6 Donor Lines

In addition to TZI8, two other lines have been identified with a very similar ANTROT-resistance QTLs on Chr06. This QTL region is similar to the region identified from PH14J described in patent application WO/2015/088970.

The two other line donors were introgressed into the susceptible line and then backcrossed three times into PH1TW8 and/or PH2SNA. Segregating populations were then scored for ANTROT as described in Example 1. The current fine mapping intervals presented below (Table 3) are our conservative intervals for these lines based on segregating individuals from multiple families.

TABLE 3

Flanking Marker Positions for Chr06 QTLs in Additional Donors.

| Donor | Genetic Interval (cM) | Physical Interval (bp) |
|---|---|---|
| Inbred A | Chr06-78.11-81.52 | 131752260-134517145 |
| PH14J | Chr06-78.11-79.52 | 131752260-134183792 |
| Inbred B | Chr06-78.11-81.52 | 131752260-134517145 |

Positions are based on the Corteva B73 genome (Version 2), and physical positions are also included for the Public B73 genome (V4).

Example 4. Transgenic Validation of NLR02 Candidate Gene

The susceptible line was transformed with constructs containing NLR02 to validate the gene. Two different constructs of NLR02 were designed: 1) a genomic insert with the native TZI8 promoter and 2) a cDNA insert with the constitutive H2B promoter.

T1 segregating seed were tested in the greenhouse (as described below) and will be tested in the field and scored for ANTSUM (as described in Example 1) to identify resistant transformants of the susceptible line. The NLR02 gene was expected to improve ANTSUM scores in the susceptible background in comparison to nulls. When introgressed into the susceptible line, (NILs) positive for the TZI8 Chr06 interval have reduced ANTROT symptoms compared to the susceptible line.

T1 seedlings segregating for the TZI8 transgene in the PH1V69 background were inoculated with ANTROT in the greenhouse using a leaf sheath assay. For the assay, seedlings were scored on a scale of 1-9 with 9 being the most resistant score and 1 being the most susceptible. Plants expressing either one or two copies of NLR02 have reduced ANTROT symptoms in the susceptible background in comparison to nulls (FIG. 2, Table 4). Arrows indicate the site of ANTROT infection (FIG. 2). T1 seed will be tested in the field as well to confirm the validation results from the greenhouse assay.

TABLE 4

PHP94983 (H2B + TZI8 CDS) Efficacy against Anthracnose Stalk Rot in the Greenhouse.

| Copy # | ANTROT (mean) | Std. Error | N | Min | Max |
|---|---|---|---|---|---|
| Overall | 6.5 | 0.37 | 65 | 1 | 9 |
| 1 | 9.0 | 0.00 | 6 | 9 | 9 |

TABLE 4-continued

PHP94983 (H2B + TZI8 CDS) Efficacy against
Anthracnose Stalk Rot in the Greenhouse.

| Copy # | ANTROT (mean) | Std. Error | N | Min | Max |
|---|---|---|---|---|---|
| 2 | 8.6 | 0.25 | 27 | 5 | 9 |
| Null | 4.4 | 0.48 | 32 | 1 | 9 |

Plants having one or two copies of the TZI8 gene (H2B+ TZI8 CDS) were more resistant to ANTROT infection in the greenhouse-based leaf sheath assay. For this assay, seedlings were scored on a scale of 1-9 with 9 being the most resistant score and 1 being the most susceptible.

Reads from an RNASeq experiment were aligned to determine if PH14J and PH1V69 have identical alleles to TZI8 for NLR02 in our Chr06 interval. PH14J has a similar predicted gene model but a unique allele with several SNPs in the predicted coding region, as confirmed by long-range PCR and Sanger sequencing. Vectors will be constructed and tested in transgenic plants to test the efficacy of the PH14J allele (SEQ ID NO: 5) of NLR02 in addition to the TZI8 allele described above.

What is claimed:

1. A method of introducing a heterologous NLR02 polynucleotide into a maize plant cell, wherein the NLR02 polynucleotide is associated with increased resistance to anthracnose stalk rot, the method comprising:
   introducing the heterologous NLR02 polynucleotide into the maize plant cell, wherein the heterologous NLR02 polynucleotide is inserted into the maize plant genome at a non-natural location and comprises a polynucleotide sequence encoding a polypeptide comprising the sequence set forth in SEQ ID NO: 2.

2. The method of claim 1, wherein the heterologous NLR02 polynucleotide comprises a polynucleotide sequence comprising at least 95% nucleic acid sequence identity to the sequence set forth in SEQ ID NO: 1 or SEQ ID NO: 3.

3. The method of claim 1, wherein the heterologous NLR02 polynucleotide comprises a polynucleotide sequence comprising the sequence set forth in SEQ ID NO: 1 or SEQ ID NO: 3.

4. The method of claim 1, further comprising regenerating a maize plant from the maize plant cell comprising the heterologous NLR02 polynucleotide inserted in the maize plant cell genome, wherein the regenerated maize plant comprises increased resistance to anthracnose stalk rot, compared to a control plant lacking the heterologous NLR02 polynucleotide.

* * * * *